(12) United States Patent
Froehlich et al.

(10) Patent No.: US 6,733,996 B2
(45) Date of Patent: May 11, 2004

(54) METHODS FOR REGULATING GENE EXPRESSION USING LIGHT

(75) Inventors: Allan C. Froehlich, Hanover, NH (US); Jennifer Loros, Thetford, VT (US); Jay C. Dunlap, Thetford Cr., VT (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 10/228,876

(22) Filed: Aug. 26, 2002

(65) Prior Publication Data

US 2004/0038400 A1 Feb. 26, 2004

(51) Int. Cl.$^7$ .................. C12P 21/02; C07K 14/37; C12N 5/00; C12N 15/11
(52) U.S. Cl. ............... 435/69.1; 435/375; 530/350; 536/24.1
(58) Field of Search .................. 435/69.1, 375; 530/350; 536/24.1

(56) References Cited

U.S. PATENT DOCUMENTS

| | | | | |
|---|---|---|---|---|
| 5,250,425 A | * | 10/1993 | Fujio et al. | 435/131 |
| 5,912,413 A | * | 6/1999 | Myers et al. | 800/205 |
| 5,985,668 A | * | 11/1999 | Mattes et al. | 435/471 |
| 6,312,920 B1 | * | 11/2001 | DeHoff et al. | 435/69.1 |

OTHER PUBLICATIONS

Ballario et al., "Roles in dimerization and blue light photoresponse of the PAS and LOV domains of Neurospora crassa white collar proteins", Mol. Microbiology 1998 29(3):719–729.
Ballario et al., "White collar–1, a central regulator of blue light response in *Neurospora*, is a zinc finger protein", The EMBO Journal 1996 15 (7): 1650–1657.
Briggs W.R., "Blue–Light Photoreceptors in Higher Plants", Annu. Rev. Cell Dev. Biol. 1999 15:33–62.
Carattoli et al., "Molecular characterization of upstream regulatory sequences controlling the photoinduced expression of the albino–3 gene of Neurospora crassa", Mol. Microbiology 1994 13 (5):787–795.
Collett et al., "Light and Clock Expression of the Neurospora Clock Gene *Frequency* Is Differentially Driven by but Dependent on WHITE COLLAR–2", Genetics 2002 160:149–158.
Crosson et al., "Structure of a flavin–binding plant photoreceptor domain:Insights into light–mediated signal transduction", Biochemistry 2001 2995–3000.
Crosthwaite et al., "Neurospora wc–1 and wc–2:Transcription, Photoresponses, and the Origins of Circadian Rhythmicity", Science 1997 276:763–769.
Denault et al., "WC–2 mediated WC–1–FRQ interaction within the PAS protein–linked circadian feedback loop of Neurospora", The EMBO Journal 2001 20 (1&2) :109–117.
Froehlich et al., "White Collar–1, a Circadian Blue Light Photoreceptor, Binding to the *frequency* Promoter", Sciencexpress 2002 1–8.
He et al., "White Collar–1, a DNA Binding transcription Factor and a Light Sensor", Sciencexpress 2002 1–5.
Linden et al., "Blue Light Regulation in *Neurospora crassa*", Fungal Genetics and Biology 1997 22:141–150.
Linden et al., "White collar 2, a partner in blue–light signal transduction, controlling expression of light–regulated genes in Neurospora crass", The EMBO Journal 1997 16(1):98–109.
Loros et al., "Genetic and Molecular Analysis of Circadian Rhythms in Neurospora", Annu. Rev. Physiol. 2001 63:757–794.

* cited by examiner

*Primary Examiner*—Terry McKelvey
(74) *Attorney, Agent, or Firm*—Licata & Tyrrell P.C.

(57) ABSTRACT

The invention provides methods of regulating gene expression using a light-activated transcription factor. The White Collar Complex, comprised of WC-1 and WC-2 proteins, binds FAD and becomes activated in the presence of light to stimulate transcription of genes operatively-linked to light-responsive regulatory sequences. Regulatory sequences and inducible regulatory system kits are also provided.

4 Claims, No Drawings

SEQUENCE LISTING

```
<160> NUMBER OF SEQ ID NOS: 29

<210> SEQ ID NO 1
<211> LENGTH: 10
<212> TYPE: DNA
<213> ORGANISM: Neurospora crassa

<400> SEQUENCE: 1
tgatgccgct                                                           10

<210> SEQ ID NO 2
<211> LENGTH: 10
```

```
<212> TYPE: DNA
<213> ORGANISM: Neurospora crassa

<400> SEQUENCE: 2
cgatgacgct                                                            10

<210> SEQ ID NO 3
<211> LENGTH: 9
<212> TYPE: DNA
<213> ORGANISM: Neurospora crassa

<400> SEQUENCE: 3 cgatccgct                                                              9

<210> SEQ ID NO 4
<211> LENGTH: 9
<212> TYPE: DNA
<213> ORGANISM: Neurospora crassa

<400> SEQUENCE: 4 cgatcccct                                                              9

<210> SEQ ID NO 5
<211> LENGTH: 11
<212> TYPE: DNA
<213> ORGANISM: Neurospora crassa

<400> SEQUENCE: 5
cgatacccgc a                                                          11

<210> SEQ ID NO 6
<211> LENGTH: 12
<212> TYPE: DNA
<213> ORGANISM: Neurospora crassa

<400> SEQUENCE: 6
cgataatacg ct                                                         12

<210> SEQ ID NO 7
<211> LENGTH: 12
<212> TYPE: DNA
<213> ORGANISM: Artificial Sequence
<220> FEATURE:
<223> OTHER INFORMATION: Consensus sequence.
<221> NAME/KEY: misc_feature
<222> LOCATION: (5)..(7)
<223> OTHER INFORMATION: "n" is defined as any nucleotide.

<400> SEQUENCE: 7
cgatnnnccg ct                                                         12

<210> SEQ ID NO 8
<211> LENGTH: 4
<212> TYPE: DNA
<213> ORGANISM: Artificial Sequence
<220> FEATURE:
<223> OTHER INFORMATION: Consensus sequence.
<221> NAME/KEY: misc_feature
<222> LOCATION: (4)..(4)
<223> OTHER INFORMATION: "n" is defined as any nucleotide.

<400> SEQUENCE: 8 gatn                                                                   4

<210> SEQ ID NO 9
```

```
<211> LENGTH: 4
<212> TYPE: DNA
<213> ORGANISM: Artificial sequence
<220> FEATURE:
<223> OTHER INFORMATION: Consensus sequence.

<400> SEQUENCE: 9 gata                                                                    4

<210> SEQ ID NO 11
<211> LENGTH: 29
<212> TYPE: DNA
<213> ORGANISM: Artificial Sequence
<220> FEATURE:
<223> OTHER INFORMATION: Synthetic oligonucleotide.

<400> SEQUENCE: 10
gggactagtc ctcatcactg cccaggttc                                        29

<210> SEQ ID NO 11
<211> LENGTH: 28
<212> TYPE: DNA
<213> ORGANISM: Artificial Sequence
<220> FEATURE:
<223> OTHER INFORMATION: Synthetic oligonucleotide.

<400> SEQUENCE: 11
gaacccggga attagacggc cgtcgcag                                         28

<210> SEQ ID NO 12
<211> LENGTH: 27
<212> TYPE: DNA
<213> ORGANISM: Artificial Sequence
<220> FEATURE:
<223> OTHER INFORMATION: Synthetic oligonucleotide.

<400> SEQUENCE: 12
ggcttaagga aaggggaggg agggcca                                          27

<210> SEQ ID NO 13
<211> LENGTH: 28
<212> TYPE: DNA
<213> ORGANISM: Artificial Sequence
<220> FEATURE:
<223> OTHER INFORMATION: Synthetic oligonucleotide.

<400> SEQUENCE: 13
gaagggcccg gaaccatggt cgcacgtc                                         28

<210> SEQ ID NO 14
<211> LENGTH: 27
<212> TYPE: DNA
<213> ORGANISM: Artificial Sequence
<220> FEATURE:
<223> OTHER INFORMATION: Synthetic oligonucleotide.

<400> SEQUENCE: 14
gggcccacta gtagctctat cttgtat                                          27

<210> SEQ ID NO 15
<211> LENGTH: 27
<212> TYPE: DNA
<213> ORGANISM: Artificial Sequence
<220> FEATURE:
<223> OTHER INFORMATION: Synthetic oligonucleotide.

<400> SEQUENCE: 15
```

```
gtattatcga tgtggcaggg caagatg                                          27

<210> SEQ ID NO 16
<211> LENGTH: 42
<212> TYPE: DNA
<213> ORGANISM: Artificial Sequence
<220> FEATURE:
<223> OTHER INFORMATION: Synthetic oligonucleotide.

<400> SEQUENCE: 16
catgccgctg caagaccgat gacgctgcaa aattgagatc ta                         42

<210> SEQ ID NO 17
<211> LENGTH: 50
<212> TYPE: DNA
<213> ORGANISM: Artificial Sequence
<220> FEATURE:
<223> OTHER INFORMATION: Synthetic oligonucleotide.

<400> SEQUENCE: 17
ctagtagatc tcaattttgc agcgtcatcg gtcttgcagc ggcatgggcc                 50

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide.

<400> SEQUENCE: 18
caagacctgc ctgaaaccg                                                   19

<210> SEQ ID NO 19
<211> LENGTH: 49
<212> TYPE: DNA
<213> ORGANISM: Artificial Sequence
<220> FEATURE:
<223> OTHER INFORMATION: Synthetic oligonucleotide.

<400> SEQUENCE: 19
taatacgact cactataggg agggatatcc tttgccctcg gacgagtgc                  49

<210> SEQ ID NO 20
<211> LENGTH: 48
<212> TYPE: DNA
<213> ORGANISM: Artificial Sequence
<220> FEATURE:
<223> OTHER INFORMATION: Synthetic oligonucleotide.

<400> SEQUENCE: 20
cgtcctgatg ccgctgcaag accgatgacg ctgcaaaatt gagatcta                   48

<210> SEQ ID NO 21
<211> LENGTH: 48
<212> TYPE: DNA
<213> ORGANISM: Artificial Sequence
<220> FEATURE:
<223> OTHER INFORMATION: Synthetic oligonucleotide.

<400> SEQUENCE: 21
tagatctcaa ttttgcagcg tcatcggtct tgcagcggca tcaggacg                   48

<210> SEQ ID NO 22
<211> LENGTH: 42
<212> TYPE: DNA
```

```
<213> ORGANISM: Artificial Sequence
<220> FEATURE:
<223> OTHER INFORMATION: Synthetic oligonucleotide.

<400> SEQUENCE: 22
caggttccag agtttggccg gacaaccagt acgggtgccc ga                    42

<210> SEQ ID NO 23
<211> LENGTH: 42
<212> TYPE: DNA
<213> ORGANISM: Artificial Sequence
<220> FEATURE:
<223> OTHER INFORMATION: Synthetic oligonucleotide.

<400> SEQUENCE: 23
tcgggcaccc gtactggttg tccggccaaa ctctggaacc tg                    42

<210> SEQ ID NO 24
<211> LENGTH: 48
<212> TYPE: DNA
<213> ORGANISM: Artificial Sequence
<220> FEATURE:
<223> OTHER INFORMATION: Synthetic oligonucleotide.

<400> SEQUENCE: 24
cgtccttcct ccgctgcaag acctctcacg ctgcaaaatt gagatcta              48

<210> SEQ ID NO 25
<211> LENGTH: 48
<212> TYPE: DNA
<213> ORGANISM: Artificial Sequence
<220> FEATURE:
<223> OTHER INFORMATION: Synthetic oligonucleotide.

<400> SEQUENCE: 25
tagatctcaa ttttgcagcg tgagaggtct tgcagcggag gaaggacg              48

<210> SEQ ID NO 26
<211> LENGTH: 43
<212> TYPE: DNA
<213> ORGANISM: Artificial Sequence
<220> FEATURE:
<223> OTHER INFORMATION: Synthetic oligonucleotide.

<400> SEQUENCE: 26
cgcagaggac cctgaacttt tcgatccgct cgatcccctg gaa                   43

<210> SEQ ID NO 27
<211> LENGTH: 51
<212> TYPE: DNA
<213> ORGANISM: Artificial Sequence
<220> FEATURE:
<223> OTHER INFORMATION: Sythetic oligonucleotide.

<400> SEQUENCE: 27
ctagttccag gggatcgagc ggatcgaaaa gttcagggtc ctctgcgggc c          51

<210> SEQ ID NO 28
<211> LENGTH: 43
<212> TYPE: DNA
<213> ORGANISM: Artificial Sequence
<220> FEATURE:
<223> OTHER INFORMATION: Synthetic oligonucleotide.

<400> SEQUENCE: 28
cgcagaggac cctgaacttt tctcctcgct ctcctccctg gaa                   43
```

```
<210> SEQ ID NO 29
<211> LENGTH: 43
<212> TYPE: DNA
<213> ORGANISM: Artificial Sequence
<220> FEATURE:
<223> OTHER INFORMATION: Synthetic oligonucleotide.

<400> SEQUENCE: 29
ttccagggag gagagcgagg agaaaagttc agggtcctct gcg         43
```

METHODS FOR REGULATING GENE EXPRESSION USING LIGHT

INTRODUCTION

This invention was made in the course of research sponsored by the National Institute of Health (NIH Grant Nos. R37GM34985 and MH44651) and the National Science Foundation (NSF Grant No. MCB-0084509). The U.S. government may have certain rights in this invention.

BACKGROUND OF THE INVENTION

Light provides essential phase information for all circadian systems, and it has been asserted that rhythms evolved from PAS/LOV domain-mediated light responses (Crosthwaite, et al. (1997) *Science* 276:763). A bacteriophytochrome mediates light input in cyanobacteia (Thresher, et al. (1998) *Science* 282:1490), while phytochromes and cryptochromes play this role in plants (Harmer, et al. (2001) *Annu. Rev. Cell Dev. Biol.* 17:215). Insect clocks use cryptochrome with additional input from opsin-based pigments in the compound eye (Harmer, et al. (2001) *Annu. Rev. Cell Dev. Biol.* 17:215); in mammals, cryptochromes may sense light (Thresher, et al. (1998) *Science* 282:1490) but recent work has focused on melanopsin as the mammalian circadian photoreceptor (Provencio, et al. (2000) *J. Neurosci.* 20:600; Hattar, et al. (2002) *Science* 295:1065; Berson, et al. (2002) *Science* 295:1070).

In Neurospora, a wide range of processes is light sensitive, including suppression and phase shifting of circadian rhythms, phototropism of perithecial beaks (Linden, et al. (1997) *Fungal Genet. Biol.* 22:141), and carotenoid biosynthesis (Payen (1843) *Ann. Chim. Phys.* 9:5). Until recently, the photoreceptor(s) involved in these blue light-influenced processes had not been identified, but screens in Neurospora for mutants involved in light perception and signaling repeatedly turned up two indispensable loci, wc-1 and wc-2 (Linden, et al. (1997) *Mol. Gen. Genet.* 254:111). WC-1 and WC-2 are nuclear transcription factors containing trans-activation and zinc-finger (Zn-finger) DNA binding domains (Ballario, et al. (1996) *EMBO J.* 15:1650; Linden and Macino (1997) *EMBO J.* 16:98). They form a White Collar Complex (WCC) by heterodimerizing via PAS (PER ARNT SIM) domains (Ballario, et al. (1998) *Mol. Microbiol.* 29:719; Denault, et al. (2001) *EMBO J.* 20:109) and act as positive elements in light signaling through direct binding of DNA (Ballario, et al. (1996) *EMBO J.* 15:1650; Linden and Macino (1997) *EMBO J.* 16:98). In a true wc-2$^{KO}$ strain, all examined light responses are lost (Collett, et al. (2002) *Genetics* 160:149). This requirement provided evidence that either WC-1 or WC-2 is the photoreceptor, or that they both are required to mediate the response of an unidentified, or duplicated, receptor (Linden, et al. (1997) *Fungal Genet. Biol.* 22:141; Briggs (1999) *Annu. Rev. Cell Dev. Biol.* 15:33; Loros and Dunlap (2001) *Annu. Rev. Physiol.* 63:757).

Parallel investigations by Froehlich, et al. ((2002) *Science* 297(5582):815–819) and He, et al. ((2002) *Science* 297(5582):840–843) reveal that WC-1 is indeed the photoreceptor. By deleting the LOV (light, oxygen, voltage) domain of WC-1, He, et al. ((2002) *Science* 297(5582):840–843) demonstrate that despite near normal induction of the circadian clock gene frequency (frq) in the dark and the maintenance of WC-2 and FRQ interactions, light responses are abolished. They further demonstrate that the flavin, FAD, copurifies with the WCC and may mediate the phototransduction mechanism. Similarly, Froehlich et al. ((2002) *Science* 297(5582):815–819) performed reconstitution experiments and demonstrate that WC-1 interacts with WC-2 to bind to light responsive DNA elements. Furthermore, in the presence of FAD and light, WC-1 initiates the photoresponse event.

In Neurospora, generation of circadian rhythms is dependent on WCC-mediated rhythmic production of frq transcript and protein, both of which are central clock components (Aronson, et al. (1994) *Science* 263:1578; Garceau, et al. (1997) *Cell* 89:469). Light causes a rapid induction of frq message, the central means by which light influences the clock (Crosthwaite, et al. (1995) *Cell* 81:1003). In the absence of WC-1 or WC-2, light induction of frq is completely abolished, highlighting the central role of WC-1 and WC-2 in light input to the clock (Collett, et al. (2002) *Genetics* 160:149; Crosthwaite, et al. (1997) *Science* 276:763). Other loci also regulated by WCC include al-1 and con-10 (Li and Schmidhauser (1995) *Dev. Biol.* 169:90–95; Linden, et al. (1997) *Mol. Gen. Genet.* 254:111–118; Linden, et al. (1997) *EMBO J.* 16:98–109).

Current methods of controlling gene expression include inducible promoters, such as those responsive to heavy metal ions (Mayo, et al. (1982) *Cell* 29:99–108; Brinster, et al. (1982) *Nature* 296:39–42; Searle, et al. (1985) *Mol. Cell. Biol.* 5:1480–1489), heat shock (Nouer, et al. (1991) in Heat Shock Response, ed. Nouer, CRC, Boca Raton, Fla., pp. 167–220), hormones (Lee, et al. (1981) *Nature* 294:228–232; Hynes, et al. (1981) *Proc. Natl. Acad. Sci. USA* 78:2038–2042; Klock, et al. (1987) *Nature* 329:734–736; Israel and Kaufman (1989) *Nucl. Acids Res.* 17:2589–2604), or drugs such as tetracycline (Gatz, et al. (1992) *Plant J.* 2:397–404; U.S. Pat. No. 5,814,618) or IPTG (Labow, et al. (1990) *Mol. Cell. Biol.* 10:3343–3356; Baim, et al. (1991) *Proc. Natl. Acad. Sci. USA* 88:5072–5076). However, these systems have generally suffered from exogenous inducer molecules (e.g., heavy metal ions, heat shock or steroid hormones) evoking pleiotropic effects, which can complicate analyses. The present invention provides a system of regulating gene expression using the readily available, inexpensive, non-toxic inducer, light.

SUMMARY OF THE INVENTION

This invention relates to methods of regulating gene expression using components of the Neurospora light-responsive White Collar Complex (WCC). In particular, this invention provides a WC-1/WC-2 transactivator which when bound to the flavin cofactor, FAD, is useful for regulating expression, in the presence of light, of a gene operatively-linked to one or more light-responsive regulatory sequences. The invention further provides light-responsive regulatory sequences which bind the WC-1/WC-2 transactivator.

These and other aspects of the present invention are set forth in more detail in the following description of the invention.

DETAILED DESCRIPTION OF THE INVENTION

The present invention provides methods, nucleic acid molecules and proteins for the regulation of gene expression in cells or organisms in a highly controlled manner. Regulation of gene expression by the system of the invention involves at least two components: A gene which is operatively-linked to a regulatory sequence and a transcriptional activator which binds to the regulatory sequence and activates transcription of the gene.

The system of the invention utilizes components of the White Collar Complex of Neurospora to stimulate gene expression in cells using light as an inducer. The White Collar complex is comprised of two proteins, WC-1 and WC-2. When in the presence of the cofactor FAD, the WCC is able to absorb light and subsequently activate transcription of a gene operatively-linked to a light-responsive regulatory sequence which interacts with WCC. Thus, in a host cell, transcription of a gene, operatively-linked to one or more light-responsive regulatory sequences, is stimulated by WC-1/WC-2 by altering the fluence or wavelength of light exposed to the host cell.

Kits which contain the components of the regulatory system described herein, are also encompassed by the invention.

The frq promoter was fused to a reporter gene, hph, and the resulting construct, pYL40B, was transformed into a frq+ strain. Light treatment of transformants resulted in a marked increase in hph transcript level, similar to that of frq. Because only the frq promoter sequence was fused to hph, it was determined that light induction of the hph transcript, and consequently of endogenous frq message, is controlled at the transcriptional level.

Cis-acting elements mediating light induction of frq were identified by transforming frq promoter deletion constructs into a frq$^{KO}$ strain and testing for light induction of frq message. Deletion of two light-responsive regulatory sequences, also referred to herein as light-responsive elements (LRES), in the frq promoter decreased light induction of frq message. A ~50% reduction was measured with the distal LRE deleted (strain AF26) and a ~70% reduction with the proximal LRE deleted (strain AF33). Deletion of both LREs (strain AF36) abolished light induction of frq, which indicated that light induction of frq is controlled entirely at the transcriptional level. Both LREs were also sufficient to confer light inducibility on an hph reporter construct (pAF35), both individually (pAF43 and pAF44) and together (pAF45).

The effects of the LRE deletions on circadian clock function were determined using race tubes to monitor Neurospora's rhythmic conidiation (Loros and Dunlap (2001) *Annu. Rev. Physiol.* 63:757). In a wild-type strain, transferring race tubes from light to dark results in a decrease in frq transcript that sets the clock to subjective dusk, after which the clock continues to run (Loros and Dunlap (2001) *Annu. Rev. Physiol.* 63:757; Crosthwaite, et al. (1995) *Cell* 81:1003). Control ABC1 transformants containing the entire frq locus displayed a period and phase similar to those of the wild-type (McClung, et al. (1989) *Nature* 339:558). The proximal LRE deletion strain (AF33) displayed a wild-type period, but the phase was dramatically changed, with the first strong peak in conidiation ~24 hours after transfer to constant darkness (DD24), ~12 hours later than occurred in the wild-type. At the molecular level, loss of the proximal LRE resulted in a stark reduction in frq mRNA and in the protein products of frq (FRQ) in continuous light (DD0) relative to wild-type (Collett, et al. (2002) *Genetics* 160:149; Crosthwaite, et al. (1995) *Cell* 81:1003). Upon transfer to DD, the low levels of frq and FRQ were interpreted as subjective dawn instead of subjective dusk, thereby causing the ~12-hour phase difference. The proximal LRE is therefore necessary for maintaining elevated levels of frq and FRQ in prolonged light as well as for eliciting the initial, rapid, light-induced increase in frq transcript. Using temperature instead of light as the entraining signal (Francis and Sargent (1979) *Plant Physiol.* 64:1000; Liu, et al. (1998) *Science* 281:825), the first peak in conidiation of both the wild-type and proximal deletion strains occurred, as expected, around DD22, indicating that deletion of the frq proximal LRE specifically affects light input to the Neurospora clock.

The distal LRE deletion strain, AF26, is arrhythmic on race tubes using either light or temperature as the entraining signal. The arrhythmicity occurs because the distal LRE plays a second role as the cis-acting element mediating the WCC-driven rhythmic frq expression that is essential for overt rhythmicity (Aronson, et al. (1994) *Science* 263:1578).

Electrophoretic mobility shift assays (EMSAs) were used to identify the trans-acting factors that specifically interact with the frq LREs. Tests for LRE binding using nuclear protein extracts and radiolabeled LRE oligonucleotide probes revealed the formation of two distinct complexes for each LRE. A faster migrating complex was seen using extracts from dark grown cultures and a slower migrating complex was seen using extracts from light-treated cultures. Specificity of the complexes was demonstrated by competition using unlabeled LRE DNA, and by noncompetition for binding by unrelated or mutated DNA sequences.

The addition of either WC-1- or WC-2-specific antiserum to a binding reaction resulted in a supershift of the complex consistent with the presence of both WC-1 and WC-2 in the complex. This supershift was seen for both the dark- and light-induced complexes using either the distal or proximal LRE; preimmune sera had no effect. The presence of WC-1 and WC-2 in the LRE-bound complexes was confirmed by the absence of complexes in binding reactions performed using nuclear protein extracts from wc-1$^{ER45}$ (loss-of-function) or wc-2$^{KO}$ strains (Collett, et al. (2002) *Genetics* 160:149). The presence of both WC-1 and WC-2 in the complexes correlates well with previous studies that revealed WC-1 and WC-2 heterodimeric complex in vitro (Ballario, et al. (1998) *Mol. Microbiol.* 29:719) and in vivo (Denault, et al. (2001) *EMBO J.* 20:109). Because WC-1 and WC-2 are known to complex with FRQ (Denault, et al. (2001) *EMBO J.* 20:109; Cheng, et al. (2001) *EMBO J.* 20:101; Merrow, et al. (2001) *EMBO J.* 20:307), the presence of FRQ in the complexes bound to the LREs was also determined using FRQ antiserum and extracts from an frq$^{KO}$ strain. FRQ was not in the dark- or light-induced complexes bound to the LREs, nor was FRQ necessary for the formation of the complexes.

Two imperfect repeats were found in the distal (TGATGCCGCT, SEQ ID NO:1 and CGATGACGCT, SEQ ID NO:2) and proximal (CGATCCGCT, SEQ ID NO:3 and CGATCCCCT, SEQ ID NO:4) LREs and compared to the LRE from another Neurospora light-induced gene, al-3 (CGATACCCGCA, SEQ ID NO:5 and CGATAATACGCT, SEQ ID NO:6) (Carattoli, et al. (1994) *Mol. Microbiol.* 13:787). The comparison revealed a consensus sequence CGATNNNCCGCT (SEQ ID NO:7), with the GATN sequence (SEQ ID NO:8) present and necessary for binding of WC-1/WC-2 to the al-3 LREs (Ballario, et al. (1996) *EMBO J.* 15:1650; Linden and Macino (1997) *EMBO J.* 16:98) and both the proximal and distal LREs of frq. The presence of the two GATN sequence repeats (SEQ ID NO:8) in the LREs is consistent with WC-1 and WC-2 binding as a heterodimer with the Zn-finger of each WC interacting with one GATN (SEQ ID NO:8). Although these Zn-finger DNA binding proteins are often referred to as GATA factors, the GATA sequence (SEQ ID NO:9) is altered within this consensus.

Extracts from dark-grown cultures retained light sensitivity in vitro, forming the slower migrating "light" complex even when exposed to light hours after extraction in the dark. Protein extractions, binding reactions, and gel electrophoresis were conducted under red lights. These wavelengths (>550 nm) are not detectable by Neurospora and by extension did not affect extracts in vitro. In vitro light sensitivity of the extracts indicated that all factors required for light perception and signal transduction to the DNA-bound WCC were soluble nuclear factors.

A dose-response curve was generated by exposing aliquots of identical, dark-grown extracts to white light ranging from 0 to 18,000 μmol photons/$M^2$ before executing the binding reactions (Table 1).

TABLE 1

| Light (μmol photons/$m^2$) | Average amount of slower migrating complex | Average amount of faster migrating complex |
| --- | --- | --- |
| 0 | 0.02 ± 0.01 | 0.95 ± 0.04 |
| 10 | 0.02 ± 0.01 | 0.92 ± 0.04 |
| 20 | 0.01 ± 0.01 | 0.80 ± 0.04 |
| 30 | 0.02 ± 0.01 | 0.76 ± 0.05 |
| 40 | 0.03 ± 0.01 | 0.77 ± 0.04 |
| 60 | 0.05 ± 0.01 | 0.77 ± 0.08 |
| 180 | 0.16 ± 0.02 | 0.77 ± 0.01 |
| 300 | 0.27 ± 0.03 | 0.63 ± 0.07 |
| 600 | 0.45 ± 0.04 | 0.40 ± 0.04 |
| 900 | 0.61 ± 0.04 | 0.29 ± 0.03 |
| 1200 | 0.69 ± 0.05 | 0.21 ± 0.03 |
| 1800 | 0.80 ± 0.05 | 0.14 ± 0.04 |
| 2700 | 0.84 ± 0.03 | 0.04 ± 0.02 |
| 3600 | 0.86 ± 0.05 | 0.03 ± 0.02 |
| 9000 | 0.93 ± 0.05 | 0.03 ± 0.01 |
| 18000 | 0.91 ± 0.06 | 0.04 ± 0.02 |

Amounts represent densitometric analysis of WCC/LRE complexes. The highest value in each group was set to one, n = 3 ± SEM.

Amounts represent densitometric analysis of WCC/LRE complexes. The highest value in each group was set to one, n=3±SEM.

As the amount of light increased, a gradual shift was seen from the faster migrating complex initially present in dark extracts to the slower migrating light-induced complex. A significant change (p<0.05, unpaired t-test) in the dark and light complexes occurred at 20 and 60 μmol photons/$m^2$, respectively, in close agreement with previously published in vivo data showing a threshold for circadian clock responses at ~8 to 24 μmol photons/$m^2$ (Crosthwaite, et al. (1995) *Cell* 81:1003; Dharmananda, (1980) thesis, University of California, Santa Cruz). Extracts given identical light treatments more than 30 minutes apart generated the same amount of light-shifted complex, indicating that the light complex, once formed in vitro, is stable.

A dose-response curve was generated to demonstrate the effect of light on the expression of frq. Cells were exposed to white light ranging from 0 to 9000 μmol photons/$m^2$ 15 minutes before isolating RNA. Relative RNA levels were determined by quantitative reverse transcriptase PCR analysis. Likewise, expression from the al-1 locus was examined as al-1 is also regulated by the WCC (Li and Schmidhauser (1995) *Dev. Biol.* 169:90–95; Linden, et al. (1997) *Mol. Gen. Genet.* 254:111–118; Linden, et al. (1997) *EMBO J.* 16:98–109). The results of this analysis indicated that a significant change in frq and al-1 expression occurred between 20 and 75 μmol photons/$m^2$/s and 150 and 600 μmol photons/$m^2$/s, respectively. Furthermore, frq expression was not significantly affected by providing to the cells light at a rate greater than 150 μmol photons/$m^2$/s (Table 2).

TABLE 2

| Photons μmol/$m^2$/s | Relative al-1 RNA ± Stdev | Relative frq RNA ± Stdev |
| --- | --- | --- |
| 0 | 1.00 ± 0.00[#] | 1.00 ± 0.00* |
| 2.5 | 1.17 ± ND | 0.68 ± ND |
| 5.0 | 1.10 ± 0.56[#] | 1.46 ± 0.10* |
| 10 | 1.84 ± ND | 2.31 ± ND |
| 20 | 1.15 ± 0.19[#] | 3.09 ± 0.21* |
| 75 | 1.49 ± 0.21[#] | 11.64 ± 3.66* |
| 150 | 5.10 ± 0.81[#] | 16.23 ± 1.51* |
| 600 | 28.66 ± 5.03[#] | 16.14 ± 3.26[#] |
| 900 | 46.49 ± 13.04[#] | 18.78 ± 5.23* |
| 1500 | 85.79 ± 2.31[#] | 20.54 ± 2.90* |
| 3000 | 110.86 ± 1.90[#] | 17.09 ± 1.57* |
| 6000 | 110.05 ± 1.09[#] | 18.01 ± 0.62[#] |
| 9000 | 114.56 ± ND | 15.78 ± ND |

*Relative RNA was the average of three experiments.
[#]Relative RNA was the average of two experiments. ND = not determined.

An equal-intensity action spectrum was generated by exposing aliquots of identical, dark-grown extracts to the same fluence of light at wavelengths varying from 410 to 540 nm before executing a series of binding reactions (Table 3).

TABLE 3

| Wavelength (nm) | Average amount of slower migrating complex ± SEM |
| --- | --- |
| 410 | 0.66 ± 0.06 |
| 415 | 0.67 ± 0.06 |
| 420 | 0.65 ± 0.08 |
| 425 | 0.72 ± 0.06 |
| 430 | 0.86 ± 0.01 |
| 435 | 0.91 ± 0.03 |
| 440 | 0.91 ± 0.05 |
| 445 | 0.86 ± 0.04 |
| 450 | 1.01 ± 0.04 |
| 455 | 1.03 ± 0.03 |
| 460 | 0.90 ± 0.02 |
| 465 | 0.89 ± 0.03 |
| 470 | 1.03 ± 0.07 |
| 475 | 0.81 ± 0.07 |
| 480 | 0.88 ± 0.02 |
| 490 | 0.60 ± 0.03 |
| 500 | 0.19 ± 0.01 |
| 510 | 0.06 ± 0.01 |
| 520 | 0.05 ± 0.02 |
| 540 | 0.03 ± 0.02 |

Amounts represent densitometric analysis. n = 3 ± SEM.

The in vitro action spectrum revealed a peak in sensitivity around 455 to 470 nm and no response to wavelengths above 520 nm. This in vitro action spectrum is in close agreement with previously published in vivo data for circadian clock responses that identified a photoreceptor with a peak at ~465 nm, no response to wavelengths above 520 nm, and sensitivity extending into the ultraviolet range (Dharmananda, (1980) thesis, University of California, Santa Cruz; Sargent and Briggs (1967) *Plant Physiol.* 42:1504). The close agreement among in vivo light studies, the in vitro action spectrum, and the in vivo and in vitro dose-response curves indicates that the in vitro light shift is a true reflection of the in vivo light responsiveness of Neurospora, that of a blue-light photoreceptor, flavin-based, with peak activity at ~465 nm and no response above 520 nm.

Cells were exposed to red (660 nm) and blue (450) light to determine the effect that wavelength had on the expression of frq, al-1, and con-10. After exposure to light, RNA was isolated from the cells and relative RNA levels were determined by quantitative reverse transcriptase PCR analysis. Control of gene expression by WCC was shown to be tightly regulated under red light and highly inducible under blue light (Table 4).

TABLE 4

| Treatment | Relative frq RNA | Relative al-1 RNA | Relative con-10 RNA |
| --- | --- | --- | --- |
| Dark | 1.00 | 1.00 | 1.00 |
| Red (660 nm) | 1.03 | 1.12 | 2.64 |
| Blue (450 nm) | 7.92 | 269.66 | 95.01 |

WC-1 contains a LOV domain, a subgroup of the PAS domain family associated with environmental sensing of cues that include light, oxygen, and voltage (Briggs (1999) *Annu. Rev. Cell Dev. Biol.* 15:33). Recently, the crystal structure of a light-sensing LOV domain from the chimeric fern photoreceptor PHY3 revealed 11 residues that interact with the chromophore, flavin mononucleotide (FMN) (Crosson and Moffat (2001) *Proc. Natl. Acad. Sci. USA* 98:2995). These 11 residues are conserved in the WC-1 LOV domain, and the high degree of overall sequence conservation (Crosson and Moffat (2001) *Proc. Natl. Acad. Sci. USA* 98:2995) indicated that the WC-1 LOV domain may exhibit the same overall secondary structure as the PHY3 LOV domain, sharing a common mechanism for flavin binding and light sensing. Further findings indicating that the WC-1 LOV domain i s involved in light-sensing include four "blind" alleles of WC-1 exist, each with a single point mutation in one of the putative 11 FMN-binding residues (Ballario, et al. (1998) *Mol. Microbiol.* 29:719), and the observation that bacterially-expressed WC-1 co-purifies with a yellow pigment, indicative of a flavin. Additionally, flavin-deficient mutants of Neurospora, rib-1, and rib-2, have greatly reduced photosensitivity for phase-shifting and carotenogenesis (Paietta and Sargent (1981) *Proc. Natl. Acad. Sci. USA* 78:5573; Paietta and Sargent (1983) *Plant Physiol.* 72:764).

In vitro coupled transcription/translation was conducted to produce WC-1 and WC-2 proteins for subsequent use in binding reactions. WC-1 and WC-2 together were able to bind to the LREs as not just one, but two distinct complexes with mobilities similar to those seen using nuclear extracts. This finding indicated that the light and dark complexes consisted exclusively of WC-1 and WC-2. These complexes were not seen when either protein was used alone or when unprogrammed lysate was used. Sucrose gradient data further demonstrated that the dark complex contained only WC-1 and WC-2, because the WCs from dark nuclear extracts co-migrated on gradients at the approximate size of a WC-1/WC-2 dimer.

No difference in binding was measured between WC proteins which were translated under dim, red lights and treated with or without light, indicating that the expressed proteins were missing a necessary cofactor (Table 5).

TABLE 5

| Treatment | Average amount of faster migrating complex ± SEM | Average amount of slower migrating complex ± SEM |
| --- | --- | --- |
| Dark −FAD | 267441 ± 10298 | 106817 ± 2047 |
| Light −FAD | 265142 ± 9164 | 108394 ± 3817 |
| Dark +FAD | 334119 ± 43086 | 56912 ± 3055 |
| Light +FAD | 264723 ± 22687 | 237163 ± 9706 |

In vitro translation experiments and subsequent binding reactions were repeated, this time adding FMN or flavin adenine dinucleotide (FAD) to the WC-1 translation reaction. FAD is the flavin cofactor for both the blue light-sensing cryptochromes (Cashmore, et al. (1999) *Science* 284:760) and the Euglena photoactivated adenyl cyclase (Iseki, et al. (2001) *Nature* 415:1047).

No light regulation of binding was found when FMN was added. However, addition of FAD conferred light sensitivity to the in vitro-translated proteins, indicating that all components necessary and sufficient for a light response were present. When FAD was combined with WC-1 and WC-2, light caused a marked increase in the amount of slower migrating complex relative to the reactions not treated with light. Furthermore, a marked increase in the slower migrating complex was observed, as compared to reactions lacking FAD treated with or without light. Additionally, FAD resulted in more of the faster migrating complex in the dark-treated relative to the light-treated/FAD reactions or the reactions minus FAD, with or without light. Taken together, these results indicate that, in the absence of FAD, the WCC can form both the faster, dark complex and the slower, light complex, but that light has no effect on the amount of either complex formed. The addition of FAD confers light responsiveness to the WCC, similar to that seen with the nuclear extracts. In the dark, a faster migrating WC-1/WC-2 dimeric complex dominates, yielding in the presence of light to a larger, slower migrating WC-1/WC-2 multimeric complex. WC-1 with FAD, exposed to light in the absence of WC-2, can initiate the mobility shift when subsequently combined in the dark with WC-2. Furthermore, WC-1 can be reconstituted with free FAD after in vitro translation. Thus, it is WC-1 that is the initial active protein partner in mediating the photoresponse.

In the inducible regulatory system of the invention, transcription of a gene is activated by a transcriptional activator, also referred to herein simply as a transactivator. The transactivator of the invention is comprised of a heterodimeric complex of WC-1 and WC-2 proteins. It should be understood that in the inducible regulatory system of the invention, the WC-1 and WC-2 proteins may be co-expressed as individual proteins, however, a single WC-1/WC-2 fusion protein which-performs the function of both WC-1 and WC-2 is also contemplated herein.

A fusion protein is intended to describe at least two proteins which are operatively-linked or connected (e.g., chemically cross-linked) in such a manner that each polypeptide may serve its intended function. Typically, the two proteins are covalently attached through peptide bonds. The fusion protein is preferably produced by standard recombinant DNA techniques. For example, a DNA molecule encoding the first protein is ligated to another DNA molecule encoding the second protein, and the resultant chimeric DNA molecule is expressed in a host cell to produce the fusion protein. The DNA molecules are ligated to each other in a 5'-to-3' orientation such that, after ligation, the translational frame of the encoded proteins is not altered (i.e., the DNA molecules are ligated to each other in-frame).

Domains of WC-1 and WC-2 known to be functional when individually expressed include the PAS domain, which is involved in WC-1/WC-2 dimerization (Ballario, et al. (1998) *Mol. Microbiol.* 29:719–729) and the zinc-finger domain, which binds DNA (Ballario, et al. (1996) *EMBO J.* 15:1650–1657; Linden and Macino (1997) *EMBO J.* 16:98–109). Furthermore, LOV domains, similar to that found in WC-1, are also functional when expressed individually (Crosson and Moffat (2001) *Proc. Natl. Acad. Sci. USA* 98:2995–3000; Crosson and Moffat (2002) *Plant Cell* 14:1067–1075; Christie, et al. (1999) *Proc. Natl. Acad. Sci.*

USA 96:8779–8783). Therefore, it should be understood that one of skill in the art may insert, delete, or rearrange WC-1 and WC-2 domains to produce a recombinant protein which retains the function(s) of each domain included. For example, one may generate a WC-1/WC-2 fusion protein which contains all the necessary domains to function as a light-responsive transactivator. Furthermore, swapping the zinc-finger DNA binding domains of WC-1/WC-2 with that from another transactivator may be performed to confer light-induced expression to a new set of genes not normally regulated by light. For example, replacing the WC-1/WC-2 zinc-finger domain with that from hZAC (Varrault, et al. (1998) *Proc. Natl. Acad. Sci. USA* 95(15):8835–8840) may provide a means of inducing apoptosis and G1 arrest in a cell via exposure to light. In general, any cellular characteristic regulated at the transcriptional level may be regulated by light through WC-1/WC-2 transactivation.

In addition, the LOV domain of WC-1, which is specific for FAD, may be replaced with the LOV domain from PHY3, which binds FMN (Crosson and Moffat (2001) *Proc. Natl. Acad. Sci. USA* 98:2995). Similarly, the transcriptional activation domains of WC-1 and WC-2 may be replaced with other known transcriptional activation domains. Types of transcriptional activation domains include acidic, proline-rich, serine/threonine-rich, and glutamine-rich transcription activation domains. Examples of acidic transcriptional activation domains include the 127 C-terminal amino acids (positions 208–335) of the herpes simplex virus virion protein 16 (VP16) and amino acid residues 753–881 of GAL4. Examples of proline-rich activation domains include amino acid residues 399–499 of CTF/NF1 and amino acid residues 31–76 of AP2. Examples of serine/threonine-rich transcription activation domains include amino acid residues 1–427 of ITF1 and amino acid residues 2–451 of ITF2. Examples of glutamine-rich activation domains include amino acid residues 175–269 of Oct1 and amino acid residues 132–243 of Sp1. The amino acid sequences of each of the above described regions, and of other useful transcriptional activation domains, are disclosed in Seipel, et al. ((1992) *EMBO J.* 13:4961–4968).

Nucleic acids encoding WC-1 and WC-2 may be incorporated into a recombinant expression vector in a form suitable for expression of the proteins in a host cell. A suitable form for expression provides that the recombinant expression vector includes one or more regulatory sequences operatively-linked to the nucleic acids encoding WC-1 and WC-2 in a manner which allows for transcription of the nucleic acids into mRNA and translation of the mRNA into the protein. Regulatory sequences may include promoters, enhancers and other expression control elements (e.g., polyadenylation signals). Such regulatory sequences are known to those skilled in the art and are described in Goeddel, Gene Expression Technology: Methods in Enzymology 185, Academic Press, San Diego, Calif. (1990). It should be understood that the design of the expression vector may depend on such factors as the choice of the host cell to be transfected and/or the level of gene expression required. Furthermore, nucleic acids encoding WC-1 may be operatively-linked to a first regulatory sequence and nucleic acids encoding WC-2 operatively-linked to a second regulatory sequence on the same or separate expression vector. The first and second regulatory sequences should, however, provide expression of WC-1 and WC-2 in a coordinate manner, i.e. in the same tissue, at the same time, with similar mRNA and protein levels produced. Alternatively, an expression vector may contain a WC-1/WC-2 chimeric gene operatively-linked to one or more regulatory sequences.

Eukaryotic microbes such as Neurospora or yeast cultures may be transformed with suitable vectors containing nucleic acids encoding the transactivator. Vectors, such as those disclosed herein (see Example 2), may be used with Neurospora promoters isolated from genes such as β-tubulin, grg-1, and invertase for effective expression of the transactivator in Neurospora.

*Saccharomyces cerevisiae* is the most commonly studied lower eukaryotic host microorganism, although a number of other species are commonly available. Yeast vectors may contain an origin of replication from the 2 micron yeast plasmid or an autonomously replicating sequence (ARS), a promoter, DNA encoding the desired protein, sequences for polyadenylation and transcription termination, and a selection gene. Exemplary plasmids include YRp7 (Stinchcomb, et al. (1979) *Nature* 282:39; Kingsman, et al. (1979) *Gene* 7:141; Tschemper, et al. (1980) *Gene* 10:157), pYepSec1 (Baldari, et al. (1987) *EMBO J.* 6:229–234), pMFa (Kurjan and Herskowitz (1982) *Cell* 30:933–943), pJRY88 (Schultz, et al. (1987) *Gene* 54:113–123), and pYES2 (INVITROGEN™ Corporation, San Diego, Calif.). These plasmids contain genes such as trp1, which provides a selectable marker for a mutant strain of yeast lacking the ability to grow in the presence of tryptophan, for example ATCC No. 44076 or PEP4-1 (Jones (1977) *Genetics* 85:12). The presence of the trp1 lesion in the yeast host cell genome then provides an effective environment for detecting transformation by growth in the absence of tryptophan.

Suitable sequences for promoting transactivator expression in yeast vectors include the promoters for metallothionein, 3-phosphoglycerate kinase (Hitzeman, et al. (1980) *J. Biol. Chem.* 255:2073) or other glycolytic enzymes (Hess, et al. (1968) *J. Adv. Enzyme Reg.* 7:149; Holland, et al. (1978) *Biochemistry* 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further disclosed in EP 73,657.

In plant cells, expression systems are often derived from recombinant Ti and Ri plasmid vector systems. In the cointegrate class of shuttle vectors, the gene of interest is inserted by genetic recombination into a non-oncogenic Ti plasmid that contains both the cis-acting and transacting elements required for plant transformation. Exemplary vectors include the pMLJ1 shuttle vector (DeBlock, et al. (1984) *EMBO J.* 3:1681–1689) and the non-oncogenic Ti plasmid pGV2850 (Zambryski, et al. (1983) *EMBO J.* 2:2143–2150). In the binary system, the gene of interest is inserted into a shuttle vector containing the cis-acting elements required for plant transformation. The other necessary functions are provided in trans by the non-oncogenic Ti plasmid. Exemplary vectors include the pBIN19 shuttle vector (Bevan (1984) *Nucl. Acids Res.* 12:8711–8721) and the non-oncogenic Ti plasmid pAL4404 (Hoekema, et al. (1983) *Nature* 303:179–180).

Promoters used in plant expression systems are typically derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV).

In mammalian cells the recombinant expression vector may be a plasmid. Alternatively, a recombinant expression vector may be a virus, or a portion thereof, which allows for expression of a nucleic acid introduced into the viral nucleic acid. For example, replication-defective retroviruses, adenoviruses and adeno-associated viruses may be used. Protocols for producing recombinant retroviruses and for infecting cells in vitro or in vivo with such viruses may be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, PZIP, pWE and pEM which are well-known to those skilled in the art. Examples of suitable packaging virus lines include ψCrip, ψCre, ψ2 and ψAm. The genome of adenovirus may be manipulated such that it encodes and expresses the transactivator but is inactivated in terms of its ability to replicate in a normal lytic viral life cycle (Berkner, et al. (1988) *BioTechniques* 6:616; Rosenfeld, et al. (1991) *Science* 252:431–434; Rosenfeld, et al. (1992) *Cell* 68;143–155). Suitable adenoviral vectors derived from the adenovirus strain Ad type 5 dl324 or other strains of adenovirus (e.g., Ad2, Ad3, Ad7 etc.) are well-known to those skilled in the art. Alternatively, an adeno-associated virus vector such as that disclosed by Tratschin, et al. ((1985) *Mol. Cell. Biol.* 5:3251–3260) may be used to express the transactivator.

In mammalian expression systems, the regulatory sequences are often provided by the viral genome commonly used promoters are derived from polyoma, Adenovirus 2, cytomegalovirus and Simian Virus 40. For example, the human cytomegalovirus IE promoter (Boshart, et al. (1985) *Cell* 41:521–530), HSV-Tk promoter (McKnight, et al. (1984) *Cell* 37:253–262) and β-actin promoter (Ng, et al. (1985) *Mol. Cell. Biol.* 5:2720–2732) may be useful in the expression of the transactivator in mammalian cells. Alternatively, the regulatory sequences of the recombinant expression vector may direct expression of the transactivator preferentially in a particular cell type, i.e., tissue-specific regulatory elements can be used. Examples of tissue-specific promoters which may be used include, but are not limited to, the albumin promoter (liver-specific; Pinkert, et al. (1987) *Genes Dev.* 1:268–277), lymphoid-specific promoters (Calame and Eaton (1988) *Adv. Immunol.* 43:235–275), promoters of T cell receptors (Winoto and Baltimore (1989) *EMBO J.* 8:729–733) and immunoglobulins (Banerji, et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci USA* 86:5473–5477), pancreas-specific promoters (Edlund, et al. (1985) *Science* 230:912–916), and mammary gland-specific promoters (e.g., milk whey promoter; U.S. Pat. No. 4,873,316; EP 264,166). Developmentally-regulated promoters are also encompassed, for example the murine hox promoters (Kessel and Gruss (1990) *Science* 249:374–379) and the α-fetoprotein promoter (Camper and Tilghman (1989) *Genes Dev.* 3:537–546).

When the host cell is from an insect (e.g., *Spodoptera frugiperda* cells), expression vectors such as the baculovirus expression vector (e.g., vectors derived from *Autographa californica* MNPV, *Trichoplusia ni* MNPV, *Rachiplusia ou* MNPV, or *Galleria ou* MNPV, as described in U.S. Pat. Nos. 4,745,051 and 4,879,236) may be employed to express the WC-1/WC-2 transactivator. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

*Escherichia coli* is the most common prokaryotic expression system. Exemplary *E. coli* strains include W3110 (ATCC 27,325), *E. coli* B, *E. coli* X1776 (ATCC 31,537), and *E. coli* 294 (ATCC 31,446). *E. coli* is typically transformed using pBR322 (Bolivar, et al. (1977) *Gene* 2:95) and derivatives thereof.

Promoters most commonly used in recombinant prokaryotic expression vectors include the beta-lactamase (penicillinase) and lactose promoter systems (Chang, et al. (1978) *Nature* 275:615; Goeddel, et al. (1979) *Nature* 281:544), a tryptophan (trp) promoter system (Goeddel, et al. (1980) *Nucl. Acids Res.* 8:4057; EP 36,776) the tac promoter (De Boer, et al. (1983) *Proc. Natl. Acad. Sci. USA* 80:21) and pL of bacteriophage 1. These promoters and Shine-Dalgarno sequence may be used for efficient expression of the WC-1/WC-2 transactivator.

The transactivator of the invention is expressed in a cell by introducing nucleic acids encoding the transactivator into a host cell, wherein the nucleic acids are in a form suitable for expression of the transactivator in the host cell. For example, a recombinant expression vector of the invention, encoding the transactivator, is introduced into a host cell. Alternatively, nucleic acid encoding the transactivator which is operatively-linked to regulatory sequences (e.g., promoter sequences) but without additional vector sequences may be introduced into a host cell. As used herein, a host cell is intended to include any prokaryotic or eukaryotic cell or cell line so long as the cell or cell line is not incompatible with the protein to be expressed, the selection system chosen or the fermentation system employed. Exemplary examples of mammalian cell lines include, but are not limited to, CHO dhfr-cells (Urlaub and Chasin (1980) *Proc. Natl. Acad. Sci. USA* 77:4216–4220), 293 cells (Graham, et al. (1977) *J. Gen. Virol.* 36;59) or myeloma cells like SP2 or NSO (Galfre and Milstein (1981) *Meth. Enzymol.* 73(B):3–46).

In addition to cell lines, the invention is applicable to normal cells, such as cells to be modified for gene therapy purposes or embryonic cells modified to create a transgenic or homologous recombinant animal. Examples of cell types of particular interest for gene therapy purposes include hematopoietic stem cells, myoblasts, hepatocytes, lymphocytes, neuronal cells and skin epithelium and airway epithelium. Additionally, for transgenic or homologous recombinant animals, embryonic stem cells and fertilized oocytes can be modified to contain nucleic acids encoding the transactivator. Moreover, plant cells can be modified to create transgenic plants.

The invention is broadly applicable and encompasses non-mammalian prokaryotic and eukaryotic cells as well, including insect (e.g., *Spodoptera frugiperda*), yeast (e.g., *S. cerevisiae, Schizosaccharomyces pombe, Pichia pastoris, Kluveromyces lactis*, Hansenula Polymorpha and Candida albicans; as generally reviewed by Fleer, ((1992) *Curr. Opin. Biotech.* 3(5):486–496)), and fungal cells (*Neurospora crassa, Aspergillus nidulins, Aspergillus fumigatus*).

Nucleic acids encoding the transactivator may be introduced into a host cell by standard techniques for transforming cells. Transformation or transfection are intended to encompass all conventional techniques for introducing nucleic acid into host cells, including calcium phosphate co-precipitation, DEAE-dextran-mediated transfection, lipofection, electroporation, microinjection, polyethylene glycol-mediated transformation, viral infection, Agrobacterium-mediated transformation, cell fusion, and ballistic bombardment. Suitable methods for transforming host cells may be found in Sambrook, et al. (Molecular Cloning: A Laboratory Manual, 2nd Edition, Cold Spring Harbor Laboratory press (1989)) and other laboratory manuals.

The number of host cells transformed with a nucleic acid encoding the transactivator disclosed herein will depend, at least in part, upon the type of recombinant expression vector used and the type of transformation technique used. Nucleic acids may be introduced into a host cell transiently, or more typically, for long-term regulation of gene expression, the nucleic-acid is stably integrated into the genome of the host cell or remains as a stable episome in the host cell. Plasmid vectors introduced into mammalian cells are typically integrated into host cell DNA at only a low frequency. In order to identify these integrants, a gene that contains: a selectable marker (e.g., drug resistance) is generally introduced into the host cells along with the nucleic acids of interest. Preferred selectable markers include those which confer resistance to certain drugs, such as G418 and hygromycin. Selectable markers may be introduced on a separate plasmid from the nucleic acids of interest or introduced on the same plasmid. Host cells transfected with nucleic acids of the invention (e.g., a recombinant expression vector) and a gene for a selectable marker may be identified by selecting for cells using the selectable marker. For example, if the selectable marker encodes a gene conferring neomycin resistance, host cells which have taken up nucleic acid may be selected with G418 resistance. Cells that have incorporated the selectable marker gene will survive, while the other cells die.

A host cell transformed with nucleic acids encoding the transactivator of the invention may be further transformed with one or more nucleic acids which serve as the target for the transactivator. The target nucleic acid comprises a nucleotide sequence to be transcribed operatively-linked to at least one light-responsive regulatory sequence, also referred to herein as light-responsive sequence, provided by the invention.

Nucleic acids encoding the transactivator of the invention can be introduced into cells growing in culture in vitro by conventional transformation techniques (e.g., calcium phosphate precipitation, DEAE-dextran transfection, electroporation, etc.). Nucleic acids may also be transferred into cells in vivo, for example by application of a delivery mechanism suitable for introduction of nucleic acid into cells in vivo, such as retroviral vectors (see e.g., Ferry, et al. (1991) *Proc. Natl. Acad. Sci. USA* 88:8377–8381; Kay, et al. (1992) *Hum. Gene Ther.* 3:641–647), adenoviral vectors (see e.g., Rosenfeld (1992) *Cell* 68:143–155; Herz and Gerard (1993) *Proc. Natl. Acad. Sci. USA* 90:2812–2816), receptor-mediated DNA uptake (see e.g., Wu and Wu (1988) *J. Biol. Chem.* 263:14621; Wilson, et al. (1992) *J. Biol. Chem.* 267:963–967; U.S. Pat. No. 5,166,320), direct injection of DNA uptake (see e.g., Acsadi, et al. (1991) *Nature* 334:815–818; Wolff, et al. (1990) *Science* 247:1465–1468) or particle bombardment (see e.g., Cheng, et al. (1993) *Proc. Natl. Acad. Sci. USA* 90:4455–4459; Zelenin, et al. (1993) *FEBS Let.* 315:29–32). Thus, for gene therapy purposes, cells may be modified in vitro and administered to a subject or, alternatively, cells may be directly modified in vivo.

Nucleic acids encoding a transactivator may be transferred into a fertilized oocyte of a non-human animal to create a transgenic animal which expresses the transactivator of the invention in one or more cell types. A transgenic animal is an animal having cells that contain a transgene, wherein the transgene was introduced into the animal or an ancestor of the animal at a prenatal, e.g., an embryonic, stage. A transgene is a DNA which is integrated into the genome of a cell from which a transgenic animal develops and which remains in the genome of the mature animal, thereby directing the expression of an encoded gene product in one or more cell types or tissues of the transgenic animal. Exemplary examples of non-human animals include, but are not limited to, mice, goats, sheep, pigs, cows or other domestic farm animals. Such transgenic animals are useful, for example, for large-scale production of proteins (gene pharming) or for basic research investigations relating to determining protein function.

A transgenic animal may be created, for example, by introducing a nucleic acid encoding the transactivator, typically linked to appropriate regulatory sequences, such as a constitutive or tissue-specific enhancer, into the male pronuclei of a fertilized oocyte, e.g., by microinjection, and allowing the oocyte to develop in a pseudopregnant female foster animal. Intron sequences and polyadenylation signals may also be included in the transgene to increase the efficiency of expression of the transgene. Methods for generating transgenic animals, particularly animals such as mice, have become conventional in the art and are described, for example, in U.S. Pat. Nos. 4,736,866 and 4,870,009. A transgenic founder animal may be used to breed additional animals carrying the transgene. Transgenic animals carrying a transgene encoding the transactivator of the invention may further be bred to other transgenic animals carrying other transgenes, e.g., to a transgenic animal which contains a gene operatively-linked to a light-responsive regulatory sequence disclosed herein.

It will be appreciated that, in addition to transgenic animals, the regulatory system disclosed herein may be applied to other transgenic organisms, such as transgenic plants. Transgenic plants may be made by conventional techniques known in the art. Accordingly, the invention encompasses non-human transgenic organisms, including animals, plants, fungi, and insects that contain cells which express the transactivator of the invention (i.e., a nucleic acid encoding the transactivator is incorporated into one or more chromosomes in cells of the transgenic organism).

The invention also provides a homologous recombinant, non-human organism expressing the transactivator of the invention. The homologous recombinant organism is intended to describe an organism, e.g. animal, plant, fungus, or insect, containing a gene which has been modified by homologous recombination between the gene and a DNA molecule introduced into a cell of the organism, e.g., an embryonic cell of the animal. An organism may be created in which nucleic acids encoding the transactivator have been introduced into a specific site of the genome, i.e., the nucleic acid has homologously recombined with an endogenous gene.

To create such a homologous recombinant organism, a vector is prepared which contains DNA encoding the transactivator flanked at its 5 and 3' ends by additional nucleic acids of a gene at which homologous recombination is to occur. The additional nucleic acids flanking the transactivator sequence are of sufficient length for successful homologous recombination with the endogenous gene. Typically, several kilobases of flanking DNA both at the 5' and 3' ends are included in the vector (see e.g., Thomas and Capecchi (1987) *Cell* 51:503 for a description of homologous recombination vectors). For example, the vector is introduced into an embryonic stem cell line (e.g., by electroporation) and cells in which the introduced DNA has homologously recombined with the endogenous DNA are selected (see e.g., Li, et al. (1992) *Cell* 69:915). The selected cells are then injected into a blastocyst of an animal (e.g., a mouse) to form aggregation chimeras (see e.g., Bradley, In: Teratocarcinomas and Embryonic Stem Cells: A Practical Approach, E. J. Robertson, ed., IRL, Oxford (1987) pp.113–152). A chimeric embryo may then be implanted into a suitable pseudopregnant female foster animal and the embryo brought to term. Progeny harboring the homologously recombined DNA in their germ cells may be used to breed animals in which all cells of the animal contain the homologously recombined DNA. These germline transmission animals may further be mated to animals carrying a gene operatively-linked to at least one light-responsive regulatory sequence disclosed herein.

In addition to the homologous recombination approaches described above, enzyme-assisted site-specific integration systems are known in the art and may be applied to the components of the regulatory system of the invention to integrate a DNA molecule at a predetermined location in a second target DNA molecule. Examples of such enzyme-assisted integration systems include the Cre recombinase-lox target system (Baubonis and Sauer (1993) *Nucl. Acids Res.* 21:2025–2029; Fukushige and Sauer (1992) *Proc. Natl. Acad. Sci. USA* 89:7905–7909) and the FLP recombinase-FRT target system (Dang and Perrimon (1992) *Dev. Genet.* 13:367–375; Fiering, et al. (1993) *Proc. Natl. Acad. Sci. USA* 90:8469–8473).

The transactivator of the invention is used to regulate the transcription of a target nucleotide sequence. This target nucleotide sequence is operatively-linked to a light-responsive regulatory sequence to which the transactivator binds. Accordingly, another aspect of the invention relates to target nucleic acids comprising a nucleotide sequence to be transcribed operatively-linked to at least one light-responsive regulatory sequence. Such nucleic acids are also referred to herein as light-regulated transcription units or simply transcription units.

Within a transcription unit, the nucleotide sequence to be transcribed typically includes a minimal promoter sequence which is not itself transcribed but which serves at least in part to position the transcriptional machinery for transcription. The minimal promoter sequence is linked to the transcribed sequence in a 5'-to-3' direction (i.e., the promoter is located upstream of the transcribed sequence) to form a contiguous nucleotide sequence. The activity of such a minimal promoter is dependent upon the binding of a transcriptional activator (such as the WC-1/WC-2 transactivator) to one or more operatively-linked light-responsive regulatory sequences. An example of a minimal promoter is from the human cytomegalovirus (Boshart, et al. (1985) *Cell* 41:521–530). Preferably, nucleotide positions between about +75 to −53 and +75 to −31 are used. Other suitable minimal promoters are known in the art or may be identified by standard techniques. For example, a functional promoter which activates transcription of a contiguously-linked reporter gene (e.g., chloramphenicol acetyl transferase, β-galactosidase or luciferase) may be progressively deleted until it no longer activates expression of the reporter gene alone but rather requires the presence of an additional regulatory sequence(s)

Within a transcription unit, the target nucleotide sequence, including the transcribed nucleotide sequence and its upstream minimal promoter sequence, is operatively-linked to at least one light-responsive regulatory sequence. In a typical configuration, the light-responsive regulatory sequence(s) is operatively-linked upstream (i.e., 5') of the minimal promoter sequence at a suitable distance to allow for transcription of the target nucleotide sequence upon binding of a regulatory protein (e.g., the WC-1/WC-2 transactivator) to the light-responsive regulatory sequence. That is, the transcription unit is comprised of, in a 5'-to-3' direction: light-responsive regulatory sequence(s)→a minimal promoter→a transcribed nucleotide sequence. It will be appreciated by those skilled in the art that there is some flexibility in the permissible distance between the light-responsive regulatory sequence(s) and the minimal promoter, although typically the light-responsive regulatory sequences will be located within about 200–400 base pairs upstream of the minimal promoter.

Alternatively, since regulatory elements have been observed in the art to function downstream of sequences to be transcribed, it is likely that the light-responsive sequence(s) may be operatively-linked downstream (i.e., 3') of the transcribed nucleotide sequence. Thus, in this configuration, the transcription unit is comprised of, in a 5'-to-3' direction: a minimal promoter→a transcribed nucleotide sequence→light-responsive sequence(s). Again, it will be appreciated that there is likely to be some flexibility in the permissible distance downstream at which the light responsive sequence(s) may be linked.

The nucleotide sequence comprising the light-responsive regulatory sequence that may be used in accordance with the invention includes, but is not limited to, SEQ ID NO:1; SEQ ID NO:2; SEQ ID NO:3; and SEQ ID NO:4 and comprises the basic core sequence CGATNNNCCGCT (SEQ ID NO:7), wherein N may be present or absent and may be A, C, T or G.

A light-regulated transcription unit may further be incorporated into a recombinant vector (e.g., a plasmid or viral vector) by standard recombinant DNA techniques. The transcription unit, or recombinant vector in which it is contained, may be introduced into a host cell by standard transformation techniques, such as those described above. It should be appreciated that, after introduction of the transcription unit into a population of host cells, it may be necessary to select a host cell clone which exhibits low basal expression of the light responsive sequence-linked nucleotide sequence (i.e., selection for a host cell in which the transcription unit has integrated at a site that results in low basal expression of the light-responsive sequence-linked nucleotide sequence). Furthermore, a light-regulated transcription unit may be introduced, by procedures described above, into the genome of a non-human animal at an embryonic stage, fungal cell, insect cell, or into a plant cell to create a transgenic or homologous recombinant organism carrying the transcription unit in some or all of its cells. Again, it should be appreciated that it may be necessary to select a transgenic or homologous organism in which there is low basal expression of the light-responsive sequence-linked nucleotide sequence in cells of interest.

The target nucleotide sequence of the light-regulated transcription unit encodes a protein of interest. Thus, upon induction of transcription of the nucleotide sequence by the transactivator of the invention and translation of the resultant mRNA, the protein of interest is produced in a host cell or organism. Alternatively, the nucleotide sequence to be transcribed may encode for an active RNA molecule, e.g., an antisense RNA molecule or ribozyme. Expression of active RNA molecules in a host cell or organism may be used to regulate functions within the host (e.g., prevent the production of a protein of interest by inhibiting translation of the mRNA encoding the protein).

A transactivator of the invention may be used to regulate transcription of an exogenous nucleotide sequence introduced into the host cell or organism. An exogenous nucleotide sequence is a nucleotide sequence which is introduced into the host cell and typically is inserted into the genome of the host. The exogenous nucleotide sequence may not be present elsewhere in the genome of the host (e.g., a foreign nucleotide sequence) or may be an additional copy of a sequence which is present within the genome of the host but which is integrated at a different site in the genome. An exogenous nucleotide sequence to be transcribed and an operatively-linked light-responsive sequence(s) may be contained within a single nucleic acid molecule which is introduced into the host cell or organism.

Alternatively, the transactivator of the invention may be used to regulate transcription of an endogenous nucleotide sequence to which a light-responsive sequence(s) has been linked. An endogenous nucleotide sequence is a nucleotide sequence which is present within the genome of the host. An endogenous gene may be operatively-linked to a light-responsive sequence(s) by homologous recombination between a light responsive sequence-containing recombination vector and sequences of the endogeneous gene. For example, a homologous recombination vector may be prepared which includes at least one light-responsive sequence and a minimal promoter sequence flanked at its 3' end by sequences representing the coding region of the endogenous gene and flanked at its 5' end by sequences from the upstream region of the endogenous gene by excluding the actual promoter region of the endogenous gene. The flanking sequences are of sufficient length for successful homologous recombination of the vector DNA with the endogenous gene. Preferably, several kilobases of flanking DNA are included in the homologous recombination vector. Upon homologous recombination between the vector DNA and the endogenous gene in a host cell, a region of the endogenous promoter is replaced by the vector DNA containing one or more light-responsive sequences operatively-linked to a minimal promoter. Thus, expression of the endogenous gene is no longer under the control of its endogenous promoter but rather is placed under the control of the light-responsive sequence(s) and the minimal promoter.

Alternatively, the light-responsive sequences may be inserted elsewhere within an endogenous gene, preferably within a 5' or 3' regulatory region, via homologous recombination to create an endogenous gene whose expression may be regulated by a light-regulated transactivator described herein. For example, one or more light-responsive sequences may be inserted into a promoter or enhancer region of an endogenous gene such that promoter or enhancer function is maintained (i.e., the light-responsive sequences are introduced into a site of the promoter/enhancer region that is not critical for promoter/enhancer function). Regions within promoters or enhancers which may be altered without loss of promoter/enhancer function are known in the art for many genes or may be determined by standard techniques for analyzing critical regulatory regions. An endogenous gene having light-responsive sequences inserted into a non-critical regulatory region will retain the ability to be expressed in its normal constitutive and/or tissue-specific manner but, additionally, may be up-regulated by the WC-1/WC-2 transactivator in a controlled manner.

Expression of a light-responsive sequence-linked nucleotide sequences is regulated by a transactivator of the invention. Thus, the transactivator and the target nucleic acid are both present in a host cell or organism. The presence of both the transactivator and the target transcription unit in the same host cell or organism may be achieved in a number of different ways. For example, a host cell may be transformed with one nucleic acid of the expression system (e.g., encoding the transactivator), stably transformed cells may be selected and then the transformed cells may be re-transformed with nucleic acids corresponding to the other nucleic acid of the expression system (e.g., the target nucleic acid to be transcribed). Two distinct selectable markers may be used for selection, e.g., uptake of the first nucleic acid may be selected with G418 and uptake of the second nucleic acid may be selected with hygromycin. Alternatively, a single population of cells may be transformed with nucleic acids corresponding to both components of the system.

The two nucleic acids may be introduced into cells as two separate molecules (e.g., two different vectors). In this case, a host cell is cotransformed with the two nucleic acid molecules or successively transformed first with one nucleic acid molecule and then the other nucleic acid molecule. Alternatively, the two nucleic acids are linked (i.e., colinear) in the same molecule (e.g., a single vector). In this case, a host cell is transformed with the single nucleic acid molecule.

The host cell may be a cell cultured in vitro or a cell present in vivo (e.g., a cell targeted for gene therapy). The host cell may further be a fertilized oocyte, embryonic stem cell or any other embryonic cell used in the creation of non-human transgenic or homologous recombinant animals. Transgenic or homologous recombinant animals which comprise both nucleic acid components of the expression system may be created by introducing both nucleic acids into the same cells at an embryonic stage, or more preferably, an animal which carries one nucleic acid component of the system in its genome is mated to an animal which carries the other nucleic acid component of the system in its genome. Offspring which have inherited both nucleic acid components may then be identified by standard techniques. Similar strategies of producing transgenic plants, fungi, and insects are also contemplated.

Another aspect of the invention pertains to kits which include the components of the inducible regulatory system of the invention. Such a kit may be used to regulate the expression of a gene of interest (i.e., a nucleotide sequence of interest to be transcribed) which may be cloned into a target transcription unit. The kit may include nucleic acids encoding the transactivator. Alternatively, cells which have nucleic acids encoding the transactivator stably incorporated therein, such that the transactivator is expressed in the cell, may be provided in the kit.

The kit includes a carrier means having in close confinement therein at least two container means: a first container means which contains a first nucleic acid encoding the transactivator of the invention (e.g., a recombinant expression vector encoding the transactivator), and a second container means which contains a transactivator target nucleic acid into which a nucleotide sequence of interest may be cloned. The second nucleic acid typically comprises a cloning site for introduction of a nucleotide sequence to be transcribed, optionally including an operatively-linked minimal promoter sequence, and at least one operatively-linked light-responsive sequence. A cloning site encompasses at least one restriction endonuclease site. Typically, multiple different restriction endonuclease sites (e.g., a polylinker) are contained within the nucleic acid sequence.

To regulate expression of a nucleotide sequence of interest using the components of the kit, the nucleotide sequence is cloned into the cloning site of the target vector of the kit by conventional recombinant DNA techniques and then the first and second nucleic acids are introduced into a host cell or organism. The transactivator expressed in the host cell or organism then regulates transcription of the nucleotide sequence of interest in the presence of the inducing agent, light.

Alternatively, the kit includes a cell which is stably transfected with a nucleic acid encoding a transactivator of the invention such that the transactivator is expressed in the cell. Thus, rather than containing nucleic acid alone, the first container means described above may contain a cell line into which the first nucleic acid encoding the transactivator has been stably introduced (e.g., by stable transformation by a conventional method such as calcium phosphate precipitation or electroporation, etc.). A nucleotide sequence of interest is cloned into the cloning site of the target vector of the kit and then the target vector is introduced into the cell expressing the transactivator.

In a host cell which carries nucleic acids encoding the transactivator of the invention and a nucleotide sequence operatively-linked to the light-responsive sequence (i.e., gene of interest to be transcribed), high levels of transcription of the nucleotide sequence operatively-linked to the light-responsive sequence(s) does not occur in the absence of the inducing agent, light. The level of basal transcription of the nucleotide sequence may vary depending upon the host cell and site of integration of the sequence, but is generally quite low or even undetectable in the absence of light. In order to induce transcription in a host cell, the host cell is exposed to light at wavelengths of at least 350 nm to 500 nm, preferably about 450 to 480 nm, and more preferably about 465 nm. Furthermore, the fluence of light is at least 5 to 6000 $\mu$mol photons/m$^2$, preferably at about 150 to 1500 $\mu$mol photons/m$^2$, and more preferably at least 600 $\mu$mol photons/m$^2$. Concerning cells carrying the inducible regulatory system in vivo, it should be understood that the amount and wavelength of light may vary depending on the location of the cell in the organism. For example, a liver cell in which the inducible regulatory system is to function may not have the same light induction requirements as a cell located on the surface of an organism. Furthermore, it should be understood the there is a reciprocity between the amount of light and the duration of exposure. For example, exposure of a cell to a low fluence of light for a long period of time may yield the same total amount of light as exposure of a cell to a high fluence of light for a short period of time. Accordingly, another aspect of the invention pertains to methods for stimulating transcription of a nucleotide sequence operatively-linked to a light-responsive sequence in a host cell or organism which expresses a transactivator of the invention. The methods involve exposing the cell to light at the appropriate wavelength and fluence for an appropriate amount of time.

To induce gene expression in a cell in vitro, a cell may be exposed, for example, to 60 $\mu$mol photons/m$^2$ of light (465 nm) for 10 seconds to achieve a total amount of light of 600 $\mu$mol photons/m$^2$. To induce gene expression in vivo, cells within a subject are exposed to light, for example, by contacting the subject with a light source capable of emitting light at 465 nm with 600 $\mu$mol photons/m$^2$ to the target cell. A subject is intended to include humans and other non-human mammals including monkeys, cows, goats, sheep, dogs, cats, rabbits, rats, mice, and transgenic and homologous recombinant species thereof. Furthermore, a subject includes plants, such as transgenic plants; fungi; insects and bacteria. When light, preferably at 465 nm, is administered to a subject, the light dosage is adjusted to preferably achieve a fluence of at least 600 $\mu$mol photons/m$^2$ which is the minimal amount effective for achieving an in vivo gene induction by the transactivator. Increasing light dosage will result in an increase in gene expression.

The ability to use different fluences and wavelengths of light for varying amounts of time in this system allows one to modulate the level of expression of a light responsive sequence-linked nucleotide sequence by decreasing or increasing the fluence, decreasing or increasing the wavelength, and/or decreasing or increase the time of exposure. Thus, the expression system of the invention provides a mechanism not only for turning gene expression on or off, but also for "fine tuning" the level of gene expression at intermediate levels depending upon the wavelength, fluence and time of exposure of the inducing agent, light. Furthermore, the advantage of light is that it is generally not toxic to most organisms, is readily available, and is inexpensive.

The invention is widely applicable to a variety of situations where it is desirable to be able to turn gene expression on and off, or regulate the level of gene expression, in a rapid, efficient and controlled manner without causing pleiotropic effects or cytotoxicity. Moreover, as FAD is present in all cells as a major electron carrier in the oxidation of fuel molecules, exogenous cofactor need not be administered to activate the transcriptional regulatory system of the invention. Thus, the system of the invention has widespread applicability to the study of cellular development and differentiation in prokaryotic and eukaryotic cells, plants, fungi, insects and animals. For example, expression of oncogenes may be regulated in a controlled manner in cells to study their function. Additionally, the system may be used to regulate the expression of site-specific recombinases, such as CRE or FLP, to thereby allow for irreversible modification of the genotype of a transgenic organism under controlled conditions at a particular stage of development.

In addition, the invention may be particularly useful for gene therapy purposes, in treatments for either genetic or acquired diseases. The general approach of gene therapy involves the introduction of nucleic acid into cells such that one or more gene products encoded by the introduced genetic material are produced in the cells to restore or enhance a functional activity. For reviews on gene therapy approaches see Anderson ((1992) *Science* 256:808–813); Miller ((1992) *Nature* 357:455–460); Friedmann ((1989) *Science* 244:1275–1281); and Cournoyer, et al. ((1990) *Curr. Opin. Biotech.* 1:196–208).

To use the system of the invention for gene therapy purposes, cells of a subject in need of gene therapy are modified to contain nucleic acids encoding a transactivator of the invention in a form suitable for expression of the transactivator in the host cells and a gene of interest (e.g., for therapeutic purposes) operatively-linked to a light-responsive sequence(s). The cells of the subject may be modified ex vivo and then introduced into the subject or the cells may be directly modified in vivo as described above. Expression of the gene of interest in the cells of the subject is then stimulated by exposing the patient to light. The level of gene expression may be varied depending upon the fluence, wavelength, and length of exposure to light.

Conventional detection methods known in the art, such as an enzyme-linked immunosorbent assay, may be used to monitor the expression of the regulated protein of interest in the host cells and the light fluence, wavelength, and time may be varied until the desired level of expression of the protein of interest is achieved. Accordingly, expression of a protein of interest may be adjusted according to the medical needs of an individual, which may vary throughout the lifetime of the individual. Furthermore, the low toxicity and daily availability of light provides a unique therapeutic option for individuals requiring life-long treatment. Thus, the regulatory system of the invention offers the advantage over constitutive regulatory systems of allowing for modulation of the level of gene expression depending upon the requirements of the therapeutic situation.

Genes of particular interest to be expressed in cells of a subject for treatment of genetic or acquired diseases include those encoding adenosine deaminase, Factor VIII, Factor IX, dystrophin, β-globin, LDL receptor, CFTR, insulin, erythropoietin, anti-angiogenesis factors, glucocerebrosidase, β-glucouronidase, α1-antitrypsin, phenylalanine hydroxylase, tyrosine hydroxylase, ornithine transcarbamylase, arginosuccinate synthetase, UDP-glucuronysyl transferase, apoAl, TNF, soluble TNF receptor, interleukins (e.g., IL-2), interferons (e.g., α- or γIFN) and other cytokines and growth factors. Cells types which may be modified for gene therapy purposes include hematopoietic stem cells, myoblasts, hepatocytes, lymphocytes, skin epithelium and airway epithelium. For further descriptions of cell types, genes and methods for gene therapy see, e.g., Wilson, et al. ((1988) *Proc. Natl. Acad. Sci. USA* 85:3014–3018); Armentano, et al. ((1990) *Proc. Natl. Acad. Sci. USA* 87:6141–6145); Wolff, et al. ((1990) *Science* 247:1465–1468); Chowdhury, et al. ((1991) *Science* 254:18022–1805); Ferry, et al. ((1991) *Proc. Natl. Acad. Sci. USA* 88:8377–8381); Wilson, et al. ((1992) *J. Biol. Chem.* 267:963–967); Quantin, et al. ((1992) *Proc. Natl. Acad. Sci. USA* 89:2581–2584); Dai, et al. ((1992) *Proc. Natl. Acad. Sci. USA* 89:10892–10895); van Beusechem, et al. ((1992) *Proc. Natl. Acad. Sci. USA* 89:7640–7644); Rosenfeld, et al. ((1992) *Cell* 68:143–155); Kay, et al. ((1992) *Hum. Gene Ther.* 3:641–647); Cristiano, et al. ((1993) *Proc. Natl. Acad. Sci. USA* 90:2122–2126); Hwu, et al. ((1993) *J. Immunol.* 150:4104–4115); and Herz and Gerard ((1993) *Proc. Natl. Acad. Sci. USA* 90:2812–2816).

Gene therapy applications of particular interest in cancer treatment include overexpression of a cytokine gene (e.g., TNF-α in tumor infiltrating lymphocytes or ectopic expression of cytokines in tumor cells to induce an anti-tumor immune response at the tumor site), expression of an enzyme in tumor cells which can convert a non-toxic agent into a toxic agent, expression of tumor-specific antigens to induce an anti-tumor immune response, expression of tumor suppressor genes (e.g., p53 or Rb) in tumor cells, and expression of a multidrug resistance gene (e.g., MDR1 and/or MRP) in bone marrow cells to protect them from the toxicity of chemotherapy.

Gene therapy applications of particular interest in treatment of viral diseases include expression of trans-dominant negative viral transactivation proteins, such as trans-dominant negative tat and rev mutants for HIV or trans-dominant ICp4 mutants for HSV (see e.g., Balboni, et al. (1993) *J. Med. Virol.* 41:289–295; Liem, et al. (1993) *Hum. Gene Ther.* 4:625–634; Malim, et al. (1992) *J. Exp. Med.* 176:1197–1201; Daly, et al. (1993) *Biochemistry* 32:8945–8954; and Smith, et al. (1992) *Virology* 191:581–588), expression of trans-dominant negative envelope proteins, such as env mutants for HIV (see e.g., Steffy, et al. (1993) *J. Virol.* 67:1854–1859), intracellular expression of antibodies, or fragments thereof, directed to viral products (see e.g., Marasco, et al. (1993) *Proc. Natl. Acad. Sci. USA* 90:7889–7893) and expression of soluble viral receptors, such as soluble CD4. Additionally, the system of the invention may be used to conditionally express a suicide gene in cells, thereby allowing for elimination of the cells after they have served an intended function. For example, cells used for vaccination may be eliminated in a subject after an immune response has been generated in the subject by light-induced expression of a suicide gene in the cells of the subject.

The inducible regulatory system disclosed herein is also useful in the treatment of rheumatoid arthritis. Genes which encode gene products that inhibit the production of inflammatory cytokines (e.g., TNF, IL-1 and IL-12) may be expressed in subjects. Examples of such inhibitors include soluble forms of a receptor for the cytokine. Additionally or alternatively, the cytokines IL-10 and/or IL-4, which stimulate a protective Th2-type response, may be expressed. Moreover, a glucocorticomimetic receptor (GCMR) may be expressed.

In addition to proteinaceous gene products, gene products that are functional RNA molecules, such as anti-sense RNAs and ribozymes, may be expressed in a controlled manner in a subject for therapeutic purposes. For example, a ribozyme may be designed which discriminates between a mutated form of a gene and a wild-type gene. Accordingly, a "correct" gene (e.g., a wild-type p53 gene) may be introduced into a cell in parallel with introduction of a regulated ribozyme specific for the mutated form of the gene (e.g., a mutated endogenous p53 gene) to remove the defective mRNA expressed from the endogenous gene. This approach is particularly advantageous in situations in which a gene product from the defective gene would interfere with the action of the exogenous wild-type gene.

Furthermore, undesirable gene products, e.g., sugars or other products contributing to the flavor, color or composition of a plant product, may be antisense-suppressed using the inducible regulatory system of the invention. For example, gene suppression may be used to vary the fatty acid distribution in plants such as rapeseed, Cuphea or jojoba, to delay the ripening of fruits and vegetables, to change the organoleptic, storage, packaging, picking, and/or processing properties of fruits and vegetables, to delay the flowering or senescing of cut flowers for bouquets, or to alter flower or fruit color. Exemplary genes that may be silenced include, but are not limited to, black phenol oxidase (browning in fruit), M-methylputrescine oxidase or putrescine N-methyl transferase (to reduce nicotine, e.g., in tobacco), polygalactouronase or cellulase (to delay ripening in fruits, e.g., tomatoes), 7-methylxanthine 3-methyl transferase (to reduce caffeine, e.g., in coffee, or to reduce theophylline, e.g., in tea), chalcone synthase, phenylalanine ammonia lyase, or dehydrokaempferol hydroxylases (to alter flower color, e.g., in ornamental flowers), cinnamoyl-CoA:NADPH reductase or cinnamoyl alcohol dehydrogenase (to reduce lignin content, e.g., in pine, fir and spruce), GL1 (to block trichome development to produce "hairless" leaves or fruit, e.g., peaches), cellulase (to decrease "woody" tissue, e.g., in asparagus), Prup1 (a peach and apricot allergen), and other plant allergens (e.g., peanut and other nut allergens), the gene encoding the toxic lectin protein or alkaloid ricinine in castor beans, genes required for seed or pit production in fruit, and the like.

Large-scale production of a protein of interest may be also be accomplished using the inducible regulatory system provided herein. Using cultured cells in vitro which have been modified to contain a nucleic acid encoding a transactivator of the invention in a form suitable for expression of the transactivator in the cells arid a gene encoding the protein of interest operatively-linked to a light-responsive sequence(s). For example, mammalian, yeast or fungal cells may be modified to contain these nucleic acid components as described herein. The modified mammalian, yeast or fungal cells may then be cultured by standard fermentation techniques in the presence of light to induce expression of the gene and produce the protein of interest. Standard protein purification techniques may be used to isolate the protein of interest from the medium or from the harvested cells.

The invention also provides for large-scale production of a protein of interest in plants, such as crop plants, or animals, such as in transgenic farm animals. Advances in transgenic technology have made it possible to produce transgenic livestock, such as cattle, goats, pigs and sheep (reviewed in Wall, et al. (1992) *J. Cell. Biochem.* 49:113–120; Clark, et al. (1987) *Trends Biotech.* 5:20–24). Accordingly, transgenic livestock carrying in their genome the components of the inducible regulatory system of the invention may be constructed, wherein a gene encoding a protein of interest is operatively-linked to at least one light-responsive sequence. Gene expression, and thus protein production, is induced by exposing the transgenic animal to light. Protein production may be targeted to a particular tissue by linking the nucleic acid encoding the transactivator to an appropriate tissue-specific regulatory element(s) which limits expression of the transactivator to certain cells. For example, a mammary gland-specific regulatory element, such as the milk whey promoter (U.S. Pat. No. 4,873,316 and EP 264,166), may be linked to the transactivator transgene to limit expression of the transactivator to mammary tissue. Thus, in the presence of light, the protein of interest will be produced in the mammary tissue of the transgenic animal. The protein may be designed to be secreted into the milk of the transgenic animal, and if desired, the protein may then be isolated from the milk.

The transcriptional activator of the invention may be used to stimulate or inhibit (by antisense suppression) expression of specific genes in animals to mimic the pathophysiology of human disease to thereby create animal models of human disease. For example, in a host animal, a gene of interest thought to be involved in a disease may be placed under the transcriptional control of one or more light-responsive sequences (e.g., by homologous recombination, as described herein). Such an animal may be mated to a second animal carrying one or more transgenes encoding a transactivator to create progeny that carry both a transactivator gene and a light-regulated target sequence. Expression of the gene of interest in these progeny may be modulated using light. For example, expression of the gene of interest may be down-regulated using antisense suppression to examine the relationship between gene expression and the disease. Such an approach may be advantageous over gene "knock out" by homologous recombination to create animal models of disease, since the light-regulated system described herein allows for control over both the levels of expression of the gene of interest and the timing of when gene expression is down- or up-regulated.

The invention is described in greater detail by the following non-limiting examples.

EXAMPLE 1

Strains, Growth Conditions, and Racetube Assay

All frq promoter deletion constructs were transformed into strain 93-4 (bd; frq$^{10}$ A; his-3) and targeted to the his-3 locus, a neutral integration site. All hph reporter constructs were transformed into strain 87-74 (bd; frq$^+$ a; his-3) and targeted to the his-3 locus. The strains used for nuclear protein extractions were 87-3 (bd; frq$^+$ a), 86-1 (bd; frq$^{10}$), 241-6 (bd; wc-2$^{KO}$), and 232-4 (bd; wc-1$^{ER45}$).

General growth conditions and manipulations of Neurospora are known in the art (Crosthwaite, et al. (1997) *Science* 276:763). Liquid culture media consisted of 1× Vogel's, 2% glucose, 0.5% arginine, and 50 ng/ml biotin. Liquid culture experiments were started by resuspending conidia from 7–10 day old slants in 1 ml of medium and adding to petri dishes containing additional medium. The petri plates were then kept at 30° C. for ~24–48 hours until a confluent mycelial mat had formed. Five to ten millimeter plugs were cut from the mats and inoculated into 125 ml flasks containing 50 ml of medium. The flasks were shaken at 150 rpm and 25° C., constant light. Methods for growing rhythmic cultures are known in the art (Crosthwaite, et al. (1997) *Science* 276:763; Loros, et al. (1989) *Science* 243:385). Briefly, liquid cultures were started as described above and then transferred at staggered intervals into 25° C., constant darkness with continued shaking and then all harvested at the same time. Light treatment of liquid cultures consisted of two minutes of light (40–50 µmol photons/m$^2$/second from General Electric cool white fluorescent bulbs, F20T12.CW) 15 minutes prior to harvesting at DD24. Light intensity was measured with a LI-COR LI-189 quantum sensor. Race tube experiments were conducted using standard methods (Aronson, et al. (1994) *Science* 263:1578). The race tube media consisted of 1× Vogel's, 0.1% glucose, 0.17% arginine, 50 ng/ml biotin, and 1.5% BACTO-agar. Racetubes entrained with a LL to DD transfer were grown in LL for 24 hours at 25° C. and then shifted to DD at 25° C. Race tubes entrained with a temperature step were grown in LL for 24 hours at 25° C., shifted into DD for 24 hours at 4° C., and then shifted to 25° C. (DD). Determination of conidiation density on race tubes and calculations of period length were performed using CHRONO (Roenneberg and Taylor (2000) *Methods Enzymol.* 305:104).

EXAMPLE 2

Plasmids

The major start site of frq transcription was determined by S1 mapping and RNase protection assays and is ~1518 base pairs (bp) from the translation start site. pKAJ120, which contains the entire 8.2 kb frq locus, was the parental vector for pAF19, pYL29, pAF27, pAF26, and pAF17 (Aronson, et al. (1994) *Science* 263:1578). pABC1 was the parental vector for all other deletion constructs and was constructed by inserting the 8.2 kb ClaI fragment from pKAJ120 into the SmaI site of pBM61 (Margolin, et al. (1997) *Fungal Gen. News.* 44:34). In a 5'-to-3' orientation, the restriction sites in the frq promoter region were ClaI, MscI-5', SnaBI, NcoI, PflMI, BglII, MscI-3', and MluI. The following constructs contain exact deletions between the restriction sites indicated: pAF19 (SnaBI/NcoI), pYL29 (NcoI/BglII), pAF17 (BglII/MscI-3'), pAF23 (MscI-5'/MscI-3'), pAF24 (MscI-5'/MluI), pAF2B (MscI-3'/MluI), pAF3B (MScI-5'/NcoI, MscI-3'/MluI), pAF37 (BglII/MluI), pAF36 (NcoI/BglII, MscI-3'/MluI), pAF27 (NcoI/PflMI), and pAF26 (PflMI/BglII). pAF29 contains 50 bp more than pAF24, 5' to the MluI site. pAF33 contains 45 bp deleted 3' of the MscI-3' site.

pAF35 contains a multiple cloning site followed by an ~80 bp region spanning the Neurospora am gene TATA box ligated to the bacterial hph gene, encoding hygromycin B phosphotransferase, followed by the Aspergillus nidulans trpC 3'-UTR sequence. An ~80 bp region spanning the Neurospora am gene TATA box was PCR amplified from pal-3mtr (Carattoli, et al. (1994) *Mol. Micro.* 13:787), SpeI and ClaI sites were added, and the fragment was ligated into ClaI/SpeI-restricted pCSN44 (Staben, et al. (1989) *Fungal Gen. News.* 36:79). The resulting construct was then cut with XbaI and the liberated TATA-hph-trpC-containing fragment was ligated into the XbaI site of pBM61 (Margolin, et al. (1997) *Fungal Gen. News.* 44:34). Shorter promoter constructs containing just the distal and/or proximal light-responsive elements were also constructed. pAF43, pAF44 and pAF45 were created by inserting PCR-amplified frq promoter sequences into pAF35. The PCR primers and oligonucleotides used in these and other experiments are provided in Table 6.

TABLE 6

| Primer | SEQUENCE (5'-to-3') | SEQ ID NO: |
| --- | --- | --- |
| ACF17 | GGGACTAGTCCTCATCACTGCCCAGGTTC | SEQ ID NO:10 |
| ACF19 | GAACCCGGGAATTAGACGGCCGTCGCAG | SEQ ID NO:11 |
| ACF20 | GGCTTAAGGAAAGGGGAGGGAGGGCCA | SEQ ID NO:12 |
| ACF21 | GAAGGGCCCGGAACCATGGTCGCACGTC | SEQ ID NO:13 |
| ACF14 | GGGCCCACTAGTAGCTCTATCTTGTAT | SEQ ID NO:14 |
| ACF18 | GTATTATCGATGTGGCAGGGCAAGATG | SEQ ID NO:15 |
| ACF44 | CATGCCGCTGCAAGACCGATGACGCTGCAAAATTGAGATCTA | SEQ ID NO:16 |
| ACF45 | CTAGTAGATCTCAATTTTGCAGCGTCATCGGTCTTGCAGCGGCATGGGCC | SEQ ID NO:17 |
| ACF34 | CAAGACCTGCCTGAAACCG | SEQ ID NO:18 |
| ACF39 | TAATACGACTCACTATAGGGAGGGATATCCTTTGCCCTCGGACGAGTGC | SEQ ID NO:19 |
| ACF57 | CGTCCTGATGCCGCTGCAAGACCGATGACGCTGCAAAATTGAGATCTA | SEQ ID NO:20 |
| ACF58 | TAGATCTCAATTTTGCAGCGTCATCGGTCTTGCAGCGGCATCAGGACG | SEQ ID NO:21 |
| ACF40 | CAGGTTCCAGAGTTTGGCCGGACAACCAGTACGGGTGCCCGA | SEQ ID NO:22 |
| ACF48 | TCGGGCACCCGTACTGGTTGTCCGGCCAAACTCTGGAACCTG | SEQ ID NO:23 |
| ACF67 | CGTCCTTCCTCCGCTACAAGACCTCTCACGCTGCAAAATTGAGATCTA | SEQ ID NO:24 |
| ACF68 | TAGATCTCAATTTTGCAGCGTGAGAGGTCTTGCAGCGGAGGAAGGACG | SEQ ID NO:25 |
| ACF62 | CGCAGAGGACCCTGAACTTTTCGATCCGCTCGATCCCCTGGAA | SEQ ID NO:26 |
| ACF63 | CTAGTTCCAGGGGATCGAGCGGATCGAAAAGTTCAGGGTCCTCTGCGGGCC | SEQ ID NO:27 |
| ACF69 | CGCAGAGGACCCTGAACTTTTCTCCTCGCTCTCCTCCCTGGAA | SEQ ID NO:28 |
| ACF70 | TTCCAGGGAGGAGAGCGAGGAGAAAAGTTCAGGGTCCTCTGCG | SEQ ID NO:29 |

Primers ACF17/ACF19, ACF20/ACF21, ACF14/ACF18 were used to generate pAF43, pAF44, and pAF35/am TATA box, respectively. Oligonucleotides ACF44 and ACF45 were annealed and inserted into pAF35 to generate pAF54.

EXAMPLE 3

RNA and Protein Analyses

Western analysis was performed using standard methods (Garceau, et al. (1997) *Cell* 89:469; Lee, et al. (2000) *Science* 289:107; Denault, et al. (2001) *EMBO J.* 20:109). RNA extractions, blotting and hybridizations were also performed using well-known methods (Aronson, et al. (1994) *Science* 263:1578). frq detection is known in the art (Heintzen, et al. (2001) *Cell* 104:453). Hph detection was essentially the same as for frq except the probe used was PCR-amplified from pCSN44 with oligonucleotides ACF34 and ACF39 (Staben, et al. (1989) *Fungal Gen. News*. 36:79). Densitometry of western and northern blots was performed using NIH Image (v. 1.61).

EXAMPLE 4

Nuclear Protein Extract Preparation

Nuclei were isolated using standard methods with some modifications (Luo, et al. (1998) *EMBO J.* 17:1228).

Conidia were harvested from large slants, inoculated into liquid culture media, and shaken at 150 rpm, 25° C. The cultures were inoculated at ~5×10$^5$ cells/ml and grown for a total of 48 hours. In vivo light treatment of tissue for nuclear extracts was the same as described above for liquid cultures. Tissue was harvested, vacuum dried, frozen in liquid nitrogen, and ground to a fine powder with glass beads under liquid nitrogen using a mortar and pestle. Five grams powdered tissue was mixed with 8 ml of buffer A [1 M sorbital, 7% (w/v) FICOLL®-type70, 20% (v/v) glycerol, 5 mM Mg(AC)$_2$, 3 mM CaCl$_2$, 50 mM Tris-HCl pH 7.5, 3 mM DTT], and then incubated on ice for 5 minutes with constant stirring. The crude homogenate was then filtered through cheesecloth and 16 ml of buffer B [10% (v/v) glycerol, 5 mM Mg(AC)$_2$, 25 mM Tris-HCl pH 7.5] were slowly added with stirring. The homogenate was then layered onto 5 ml of buffer C [a solution consisting of a 2.5:4 mix of buffers A and B] in a 50 ml tube, and centrifuged at 3000×g for 7 minutes at 4° C. in a SW28 rotor to remove cell debris. The supernatant was layered onto 5 ml of buffer D [1 M sucrose, 10% (v/v) glycerol, 5 mM Mg(AC)$_2$, 25 mM Tris-HCl pH 7.5] in a 50 ml tube and centrifuged at 9400×g for 15 minutes at 4° C. to pellet the nuclei. The supernatant was discarded, and the nuclei transferred to a microcentrifuge tube and resuspended in buffer D at a 2:1 ratio (nuclei:buffer D). Extraction buffer [15 mM HEPES pH 7.9, 0.1 mM EDTA, 5 mM $MgCl_2$, 5% (v/v) glycerol, 75 mM NaCl, 20 $\mu M$ $ZnCl_2$] was slowly added to a final ratio of 1:1 (resuspended nuclei: extraction buffer) and incubated at 4° C. for 30 minutes with rocking. The nuclei suspension was then centrifuged at 16000×g for 5 minutes at 4° C. to pellet the nuclei, and the supernatant was desalted by passing over BIO-GEL® P-30 chromatography columns (BIO-RAD®, Hercules, Calif.) equilibrated with binding buffer [20 mM HEPES pH 7.9, 1 mM EDTA, 2 mM $MgCl_2$, 10% (v/v) glycerol, 20 $\mu M$ $ZnCl_2$] containing 40 mM KCl. The flow-through was centrifuged at 16000×g for 5 minutes at 4° C. to pellet insoluble proteins, and the resulting supernatant, referred to as nuclear protein extract, was aliquoted, frozen in liquid nitrogen, and stored at −80° C. All buffers contained 1 $\mu$g/ml leupeptin, 10 $\mu$g/ml pepstatin A, and 1 mM phenylmethylsulfonyl flouride (PMSF). The entire extraction was performed under red lights (fluorescent bulbs F40R RED, General Electric, Fairfield, Conn.).

EXAMPLE 5

Electrophoretic Mobility Shift Assay

The probes consisted of two oligonucleotides of equal length annealed together and end-labeled using T4 polynucleotide kinase and [$\gamma$-$^{32}$P]ATP. Unincorporated ATP was removed using a BIO-GEL® P-30 chromatography column (BIO-RAD®, Hercules, Calif.), and probe was diluted to a final concentration of 0.018 $\mu$M. Oligonucleotide pairs were annealed for use as probe or unlabeled competitor. Distal LRE probe, the unrelated 42 bp competitor, and the mutated distal LRE competitor were generated with oligonucleotide pairs ACF57/ACF58, ACF40/ACF48 and ACF67/ACF68, respectively. The proximal LRE probe and mutated proximal LRE competitor were generated with oligonucleotide pairs ACF62/ACF63 and ACF69/ACF70, respectively.

Binding reactions using nuclear protein extracts contained 1× binding buffer, 80 $\mu$M KCl, 0.1 $\mu$g poly(dI-dC), 1 $\mu$l probe, 0.5 $\mu$l of normal rabbit sera (Pocono Rabbit Farm, Canadensis, Pa.), and 3 $\mu$g of nuclear protein extract, which was added last to the binding reactions, in a total volume of 20 $\mu$l. In reactions that contained antisera, 1 $\mu$l anti-WC-1, 1 $\mu$l anti-WC-2, or 0.5 $\mu$l anti-FRQ was used. Binding reactions using in vitro translated proteins contained 1× binding buffer, 1 $\mu$g poly(dI-dC), 1 $\mu$l probe, and 6 $\mu$l of the in vitro translation reaction in a total volume of 20 $\mu$l . Binding reactions were incubated for 30 minutes on ice prior to electrophoresis at 4° C. on nondenaturing 4% polyacrylamide gels containing 0.5×TBE and 2.5% (v/v) glycerol. Gels were dried and visualized using a PhosphorImager and IMAGEQUANT® software (Molecular Dynamics, Sunnyvale, Calif.). Binding reactions and gel electrophoreses were performed under red lights.

EXAMPLE 6

In vitro Transcription/Translation

TNT®-Coupled Reticulocyte Lysate system (PROMEGA®, Madison, Wis.) was used according to the manufacturer's directions to in vitro transcribe/translate full-length WC-1 using pAF60 as template and full length WC-2 using pGEM®/WC-2 as template. 8 $\mu$M $ZnCl_2$ was added to each reaction. Where indicated, FAD (SIGMA®, St. Louis, Mo.) and FMN (SIGMA®, St. Louis, Mo.) were added to a final concentration of 1 mM. Reactions were conducted under red lights.

EXAMPLE 7

Action Spectrum and Dose Response Curve

Nuclear protein extracts used for the action spectrum and dose response curves were harvested at DD12, ~CTO. Similar results were generated using extracts from DD24 (~CT13). The light source for the in vitro dose response curve and the action spectrum was a FIBER-LITE® High Intensity Illuminator Series 180 (Dolan-Jenner, Lawrence, Mass.) with halogen bulb. A High Intensity Monochromater, (BAUSCH & LOMB®, Rochester, N.Y., cat.# 33-86-76, 33-86-25) with 500 nm blaze was used to produce the discrete wavelengths for the action spectrum with the entrance and exit slits set to allow ±5 nm around the desired wavelength. For the action spectrum, the same fluence of light, 180 $\mu$mol photons/$m^2$, was given at each wavelength tested and was used because it elicited a 50% maximal response at 450 nm, predicted to be near the wavelength of peak activity. It was important to use this 50% maximal response to ensure that the amount of light given at a particular wavelength would be below saturation and thus capable of giving a measurable response. For the dose response curve duration and intensity of the light was varied to achieve the desired doses. Reciprocity of duration and intensity was found to hold for the times and intensities used herein.

What is claimed is:

1. A method of regulating expression of a gene in a host cell comprising:

a) contacting a host cell containing FAD and a gene operatively-linked to a light-responsive regulatory sequence with a recombinant WC-1/WC-2 transactivator which binds FAD and the light-responsive regulatory sequence, and b) exposing the host cell to light to stimulate activity of the recombinant WC-1/WC-2 transactivator so that the gene operatively-linked to the light-responsive regulatory sequence is expressed.

2. The method of claim 1 wherein the light-responsive regulatory sequence comprises SEQ ID NO:7.

3. An isolated light-responsive regulatory sequence consisting of SEQ ID NO:2, SEQ ID NO:3, or SEQ ID NO:4.

4. A kit comprising a first container means which contains a recombinant WC-1/WC-2 transactivator and a second container means which contains an isolated light-responsive regulatory sequence.

* * * * *